United States Patent
Youakim et al.

(10) Patent No.: US 7,186,802 B2
(45) Date of Patent: Mar. 6, 2007

(54) CLAUDIN POLYPEPTIDES

(75) Inventors: Adel Youakim, Seattle, WA (US); Robert F. DuBose, Bellevue, WA (US); Steven R. Wiley, Seattle, WA (US)

(73) Assignee: Immunex Corporation, Thousand Oaks, CA (US)

( * ) Notice: Subject to any disclaimer, the term of this patent is extended or adjusted under 35 U.S.C. 154(b) by 0 days.

(21) Appl. No.: 10/344,487

(22) PCT Filed: Aug. 15, 2001

(86) PCT No.: PCT/US01/25662

§ 371 (c)(1),
(2), (4) Date: Jun. 27, 2003

(87) PCT Pub. No.: WO02/14499

PCT Pub. Date: Feb. 21, 2002

(65) Prior Publication Data

US 2004/0038370 A1    Feb. 26, 2004

Related U.S. Application Data

(60) Provisional application No. 60/225,794, filed on Aug. 15, 2000, provisional application No. 60/225,513, filed on Aug. 15, 2000.

(51) Int. Cl.
*C07K 1/00* (2006.01)
*G01N 33/53* (2006.01)
*A61K 38/00* (2006.01)

(52) U.S. Cl. .......................... 530/350; 435/7.1; 514/12

(58) Field of Classification Search ................ 435/6, 435/69.1, 7.1; 530/350; 514/12, 2
See application file for complete search history.

(56) References Cited

U.S. PATENT DOCUMENTS 6,416,974 B1 * 7/2002 Holtzman et al. ......... 435/69.1

2004/0033493 A1 * 2/2004 Tchernev et al. ............ 435/6

FOREIGN PATENT DOCUMENTS

WO    WO 2000/20447 A    4/2000

OTHER PUBLICATIONS

Furuse et al., A single gene product, claudin-1 or -2, reconstitutes tight junction strands and recruits occludin in fibroblasts.☐☐J Cell Biol. Oct. 19, 1998;143(2):391-401.*
Tsukita and Furuse, Occludin and claudins in tight-junction strands: leading or supporting players?☐☐Trends Cell Biol. Jul. 1999;9(7):268-73. Review.*
Konrad M., Applications of genetic engineering to the pharmaceutical industry, 1983, Ann N Y Acad Sci., vol. 413, abstract.*
Mahairas et al., EMBL Database Accession No. AQ612838, Jun. 21, 1999.
Mahairas et al., EMBL Database Accession No. AQ229039, Sep. 28, 1998.
Morita et al., "Claudin multigene family encoding four-transmembrane domain protein components of tight junction strands", *Proc Natl Acad Sci USA* 96(2): 511-516, Jan. 19, 1999.
Furuse et al., "Claudin-1 and -2: novel integral membrane proteins localizing at tight junctions with no sequence similarity to Occludin", *J Cell Biol* 141(7): 1539-1550, Jun. 29, 1998.

* cited by examiner

*Primary Examiner*—Ponnathapu Achutamurthy
*Assistant Examiner*—Robert B. Mondesi
(74) *Attorney, Agent, or Firm*—Suzanne A. Sprunger; Susan E. Lingenfelter

(57) ABSTRACT

This invention relates to new members of the human Claudin polypeptide family, to methods of making such polypeptides, and to methods of using them to treat Claudin-associated conditions and to identify compounds that alter Claudin polypeptide activities.

3 Claims, No Drawings

SEQUENCE LISTING

<160> NUMBER OF SEQ ID NOS: 13

<210> SEQ ID NO 1
<211> LENGTH: 111
<212> TYPE: PRT
<213> ORGANISM: Homo sapiens

<400> SEQUENCE: 1

```
Met Gly Leu Trp Gln Thr Cys Val Ile Gln Glu Glu Val Gly Met Gln
1               5                   10                  15

Cys Lys Asp Phe Asp Ser Phe Leu Ala Leu Pro Ala Glu Leu Arg Val
            20                  25                  30
```

```
Ser Arg Ile Leu Met Phe Leu Ser Asn Gly Leu Gly Phe Leu Gly Leu
         35                  40                  45

Leu Val Ser Gly Phe Gly Leu Asp Cys Leu Arg Ile Gly Glu Ser Gln
 50                  55                  60

Arg Asp Leu Lys Arg Arg Leu Leu Ile Leu Gly Gly Ile Leu Ser Trp
65                  70                  75                  80

Ala Ser Gly Ile Thr Ala Leu Val Pro Val Ser Trp Val Ala His Lys
                 85                  90                  95

Thr Val Gln Glu Phe Trp Asp Glu Asn Val Pro Asp Phe Val Pro
            100                 105                 110

<210> SEQ ID NO 2
<211> LENGTH: 158
<212> TYPE: PRT
<213> ORGANISM: Homo sapiens

<400> SEQUENCE: 2

Met Ala Leu Ile Phe Arg Thr Ala Met Gln Ser Val Gly Leu Leu Leu
 1               5                  10                  15

Ser Phe Leu Gly Trp Ile Leu Ser Ile Ile Thr Thr Tyr Leu Pro His
                 20                  25                  30

Trp Lys Asn Leu Asn Leu Asp Leu Asn Glu Met Glu Asn Trp Thr Met
            35                  40                  45

Gly Leu Trp Gln Thr Cys Val Ile Gln Glu Val Gly Met Gln Cys
 50                  55                  60

Lys Asp Phe Asp Ser Phe Leu Ala Leu Pro Ala Glu Leu Arg Val Ser
65                  70                  75                  80

Arg Ile Leu Met Phe Leu Ser Asn Gly Leu Gly Phe Leu Gly Leu Leu
                 85                  90                  95

Val Ser Gly Phe Gly Leu Asp Cys Leu Arg Ile Gly Glu Ser Gln Arg
                100                 105                 110

Asp Leu Lys Arg Arg Leu Leu Ile Leu Gly Gly Ile Leu Ser Trp Ala
            115                 120                 125

Ser Gly Ile Thr Ala Leu Val Pro Val Ser Trp Val Ala His Lys Thr
        130                 135                 140

Val Gln Glu Phe Trp Asp Glu Asn Val Pro Asp Phe Val Pro
145                 150                 155

<210> SEQ ID NO 3
<211> LENGTH: 896
<212> TYPE: DNA
<213> ORGANISM: Homo sapiens

<400> SEQUENCE: 3
tccattatta caacttattt gccacactgg aagaacctca aacctggact taaatgaaat      60
ggaaaactgg accatgggac tctggcaaac ctgtgtcatc caagaggaag tgggatgca     120 atgcaaggac tttgactcct tcctggcttt gcctgctgaa ctcagggtct ccaggatctt     180
aatgtttctg tcaaatgggc tgggatttct gggcctgctg gtctctggt ttggcctgga      240 ctgtttgaga attggagaga gtcagagaga tctcaagagg cgactgctca ttctgggagg     300
aattctgtcc tgggcctcgg gaatcacagc cctggttccc gtctcttggg ttgcccacaa     360
gacggttcag gagttctggg atgagaacgt cccagacttt gtcccaggt gggagtttgg      420 ggaggccctg tttctgggct ggtttgctgg actttctctt ctgctaggag ggtgtctgct     480
caactgcgca gcctgctcca gccacgctcc cctagctttg ggccactatg cagtggcgca     540
```

```
aatgcaaact cagtgtccct acctggaaga tgggacagca gatcctcaag tgtaagactc    600
cgacaaggcc agagatgtat cctgtatcaa ctgtgatgac aaagacctct ttgttttgta    660
gctaaacctg tgatgctcac gttttctcat tcactatttt tctacagtag gtagacccac    720
ttccctctaa atctgaata atgaaggaaa aatcttttat ctaaaagaaa atgattatgg    780
taagcattat acaggtagaa gtgaaacaag cttcattgat ctggttattg aaattaatgt    840
ggtggctgtc caatacagtc agtttcaagc tttaatgtgt aaatttcata ttagaa       896
```

<210> SEQ ID NO 4
<211> LENGTH: 197
<212> TYPE: PRT
<213> ORGANISM: Homo sapiens

<400> SEQUENCE: 4

```
Pro Leu Leu Gln Leu Ile Cys His Thr Gly Arg Thr Ser Asn Leu Asp
1               5                   10                  15

Leu Asn Glu Met Glu Asn Trp Thr Met Gly Leu Trp Gln Thr Cys Val
            20                  25                  30

Ile Gln Glu Glu Val Gly Met Gln Cys Lys Asp Phe Asp Ser Phe Leu
        35                  40                  45

Ala Leu Pro Ala Glu Leu Arg Val Ser Arg Ile Leu Met Phe Leu Ser
    50                  55                  60

Asn Gly Leu Gly Phe Leu Gly Leu Leu Val Ser Gly Phe Gly Leu Asp
65                  70                  75                  80

Cys Leu Arg Ile Gly Glu Ser Gln Arg Asp Leu Lys Arg Arg Leu Leu
                85                  90                  95

Ile Leu Gly Gly Ile Leu Ser Trp Ala Ser Gly Ile Thr Ala Leu Val
            100                 105                 110

Pro Val Ser Trp Val Ala His Lys Thr Val Gln Glu Phe Trp Asp Glu
        115                 120                 125

Asn Val Pro Asp Phe Val Pro Arg Trp Glu Phe Gly Glu Ala Leu Phe
    130                 135                 140

Leu Gly Trp Phe Ala Gly Leu Ser Leu Leu Gly Gly Cys Leu Leu
145                 150                 155                 160

Asn Cys Ala Ala Cys Ser Ser His Ala Pro Leu Ala Leu Gly His Tyr
                165                 170                 175

Ala Val Ala Gln Met Gln Thr Gln Cys Pro Tyr Leu Glu Asp Gly Thr
            180                 185                 190

Ala Asp Pro Gln Val
        195
```

<210> SEQ ID NO 5
<211> LENGTH: 895
<212> TYPE: DNA
<213> ORGANISM: Homo sapiens

<400> SEQUENCE: 5

```
tccattatta caacttattt gccacactgg aagaacctca acctggactt aaatgaaatg    60
gaaaactgga ccatgggact ctggcaaacc tgtgtcatcc aagaggaagt ggggatgcaa    120
tgcaaggact ttgactcctt cctggctttg cctgctgaac tcagggtctc caggatctta    180
atgtttctgt caaatgggct gggatttctg ggcctgctgg tctctgggtt tggcctggac    240
tgtttgagaa ttggagagag tcagagagat ctcaagaggc gactgctcat tctgggagga    300
attctgtcct gggcctcggg aatcacagcc ctggttcccg tctcttgggt tgcccacaag    360
```

-continued

```
acggttcagg agttctggga tgagaacgtc ccagactttg tccccaggtg ggagtttggg      420
gaggccctgt ttctgggctg gtttgctgga ctttctcttc tgctaggagg gtgtctgctc      480
aactgcgcag cctgctccag ccacgctccc ctagctttgg gccactatgc agtggcgcaa      540
atgcaaactc agtgtcccta cctggaagat gggacagcag atcctcaagt gtaagactcc      600
gacaaggcca gagatgtatc ctgtatcaac tgtgatgaca agacctcttt tgttttgtag      660
ctaaacctgt gatgctcacg ttttctcatt cactatttt ctacagtagg tagacccact      720
tccctctaaa atctgaataa tgaaggaaaa atcttttatc taaaagaaaa tgattatggt      780
aagcattata caggtagaag tgaaacaagc ttcattgatc tggttattga aattaatgtg      840
gtggctgtcc aatacagtca gtttcaagct ttaatgtgta aatttcatat tagaa           895
```

<210> SEQ ID NO 6
<211> LENGTH: 220
<212> TYPE: PRT
<213> ORGANISM: Homo sapiens

<400> SEQUENCE: 6

```
Met Ala Leu Ile Phe Arg Thr Ala Met Gln Ser Val Gly Leu Leu Leu
1               5                   10                  15

Ser Phe Leu Gly Trp Ile Leu Ser Ile Ile Thr Thr Tyr Leu Pro His
            20                  25                  30

Trp Lys Asn Leu Asn Leu Asp Leu Asn Glu Met Glu Asn Trp Thr Met
        35                  40                  45

Gly Leu Trp Gln Thr Cys Val Ile Gln Glu Val Gly Met Gln Cys
    50                  55                  60

Lys Asp Phe Asp Ser Phe Leu Ala Leu Pro Ala Glu Leu Arg Val Ser
65                  70                  75                  80

Arg Ile Leu Met Phe Leu Ser Asn Gly Leu Gly Phe Leu Gly Leu Leu
                85                  90                  95

Val Ser Gly Phe Gly Leu Asp Cys Leu Arg Ile Gly Glu Ser Gln Arg
            100                 105                 110

Asp Leu Lys Arg Arg Leu Leu Ile Leu Gly Gly Ile Leu Ser Trp Ala
        115                 120                 125

Ser Gly Ile Thr Ala Leu Val Pro Val Ser Trp Val Ala His Lys Thr
    130                 135                 140

Val Gln Glu Phe Trp Asp Glu Asn Val Pro Asp Phe Val Pro Arg Trp
145                 150                 155                 160

Glu Phe Gly Glu Ala Leu Phe Leu Gly Trp Phe Ala Gly Leu Ser Leu
                165                 170                 175

Leu Leu Gly Gly Cys Leu Leu Asn Cys Ala Ala Cys Ser Ser His Ala
            180                 185                 190

Pro Leu Ala Leu Gly His Tyr Ala Val Ala Gln Met Gln Thr Gln Cys
        195                 200                 205

Pro Tyr Leu Glu Asp Gly Thr Ala Asp Pro Gln Val
    210                 215                 220
```

<210> SEQ ID NO 7
<211> LENGTH: 220
<212> TYPE: PRT
<213> ORGANISM: Mus musculus

<400> SEQUENCE: 7

```
Met Gly Leu Val Phe Arg Thr Ala Thr Gln Ala Ala Leu Leu Leu
1               5                   10                  15
```

```
Ser Leu Leu Gly Trp Val Leu Ser Cys Leu Thr Asn Tyr Leu Pro His
            20                  25                  30

Trp Lys Asn Leu Asn Leu Glu Leu Asn Glu Met Glu Asn Trp Thr Met
        35                  40                  45

Gly Leu Trp Lys Ser Cys Val Ile Gln Glu Val Gly Arg Gln Cys
    50                  55                  60

Lys Asp Phe Asp Ser Phe Leu Ala Leu Pro Ala Glu Leu Gln Val Ser
 65                  70                  75                  80

Arg Val Leu Met Ser Leu Cys Asn Gly Leu Gly Leu Gly Leu Leu
                85                  90                  95

Ala Ser Gly Cys Gly Leu Asp Cys Leu Arg Leu Gly Glu Thr Gln Glu
                100                 105                 110

Gly Leu Lys Lys Arg Leu Leu Thr Leu Gly Gly Thr Leu Leu Trp Thr
            115                 120                 125

Ser Gly Val Met Val Leu Val Pro Val Ser Trp Val Ala His Lys Thr
130                 135                 140

Val Arg Glu Phe Trp Asp Glu Thr Met Pro Glu Ile Val Pro Arg Trp
145                 150                 155                 160

Glu Phe Gly Glu Ala Leu Phe Leu Gly Trp Phe Ala Gly Phe Cys Leu
                165                 170                 175

Val Leu Gly Gly Cys Val Leu His Cys Ala Ala Cys Trp Ser Pro Ala
                180                 185                 190

Pro Ala Ser Ser His Tyr Ala Val Ala Gly Pro Arg Asp His Gln
            195                 200                 205

Gln His Leu Glu Leu Lys Gln Ala Asn Pro Glu Ile
        210                 215                 220

<210> SEQ ID NO 8
<211> LENGTH: 211
<212> TYPE: PRT
<213> ORGANISM: Homo sapiens

<400> SEQUENCE: 8

Met Ala Asn Ser Gly Leu Gln Leu Leu Gly Tyr Phe Leu Ala Leu Gly
 1               5                  10                  15

Gly Trp Val Gly Ile Ile Ala Ser Thr Ala Leu Pro Gln Trp Lys Gln
            20                  25                  30

Ser Ser Tyr Ala Gly Asp Ala Ile Ile Thr Ala Val Gly Leu Tyr Glu
        35                  40                  45

Gly Leu Trp Met Ser Cys Ala Ser Gln Ser Thr Gly Gln Val Gln Cys
    50                  55                  60

Lys Leu Tyr Asp Ser Leu Leu Ala Leu Asp Gly His Ile Gln Ser Ala
 65                  70                  75                  80

Arg Ala Leu Met Val Val Ala Val Leu Leu Gly Phe Val Ala Met Val
                85                  90                  95

Leu Ser Val Val Gly Met Lys Cys Thr Arg Val Gly Asp Ser Asn Pro
                100                 105                 110

Ile Ala Lys Gly Arg Val Ala Ile Ala Gly Gly Ala Leu Phe Ile Leu
            115                 120                 125

Ala Gly Leu Cys Thr Leu Thr Ala Val Ser Trp Tyr Ala Thr Leu Val
        130                 135                 140

Thr Gln Glu Phe Phe Asn Pro Ser Thr Pro Val Asn Ala Arg Tyr Glu
145                 150                 155                 160

Phe Gly Pro Ala Leu Phe Val Gly Trp Ala Ser Ala Gly Leu Ala Val
                165                 170                 175
```

```
Leu Gly Gly Ser Phe Leu Cys Cys Thr Cys Pro Glu Pro Glu Arg Pro
            180                 185                 190

Asn Ser Ser Pro Gln Pro Tyr Arg Pro Gly Pro Ser Ala Ala Ala Arg
        195                 200                 205

Glu Tyr Val
    210

<210> SEQ ID NO 9
<211> LENGTH: 193
<212> TYPE: PRT
<213> ORGANISM: Mus musculus

<400> SEQUENCE: 9

Tyr Phe Leu Ala Leu Gly Gly Trp Val Gly Ile Ile Ala Ser Thr Ala
1               5                   10                  15

Leu Pro Gln Trp Lys Gln Ser Ser Tyr Ala Gly Asp Ala Ile Ile Thr
            20                  25                  30

Ala Val Gly Leu Tyr Glu Gly Leu Trp Met Ser Cys Ala Ser Gln Ser
        35                  40                  45

Thr Gly Gln Val Gln Cys Lys Leu Tyr Asp Ser Leu Leu Ala Leu Asp
    50                  55                  60

Gly His Ile Gln Ser Ala Arg Ala Leu Met Val Val Ala Val Leu Leu
65                  70                  75                  80

Gly Phe Val Ala Met Val Leu Ser Val Val Gly Met Lys Cys Thr Arg
                85                  90                  95

Val Gly Asp Ser Asn Pro Thr Ala Lys Ser Arg Val Ala Ile Ser Gly
            100                 105                 110

Gly Ala Leu Phe Leu Leu Ala Gly Leu Cys Thr Leu Thr Ala Val Ser
        115                 120                 125

Trp Tyr Ala Thr Leu Val Thr Gln Glu Phe Phe Asn Pro Ser Thr Pro
    130                 135                 140

Val Asn Ala Arg Tyr Glu Phe Gly Pro Ala Leu Phe Val Gly Trp Ala
145                 150                 155                 160

Ser Ala Gly Leu Ala Met Leu Gly Gly Ser Phe Leu Cys Cys Thr Cys
                165                 170                 175

Pro Glu Pro Glu Arg Ala Asn Ser Ile Pro Gln Pro Tyr Arg Ser Gly
            180                 185                 190

Pro

<210> SEQ ID NO 10
<211> LENGTH: 69
<212> TYPE: PRT
<213> ORGANISM: Homo sapiens

<400> SEQUENCE: 10

Met Ala Asn Ser Gly Leu Gln Leu Leu Gly Tyr Phe Leu Ala Leu Gly
1               5                   10                  15

Gly Trp His Ser Pro Ala Thr Val Glu Ala Val Phe Leu Arg Arg Leu
            20                  25                  30

Thr Ala Ile Ile Thr Ala Val Gly Leu Tyr Glu Gly Leu Trp Met Ser
        35                  40                  45

Cys Ala Ser Gln Ser Thr Gly Gln Val Gln Cys Lys Leu Tyr Asp Ser
    50                  55                  60

Leu Leu Ala Leu Asp
65
```

<210> SEQ ID NO 11
<211> LENGTH: 229
<212> TYPE: PRT
<213> ORGANISM: Homo sapiens

<400> SEQUENCE: 11

```
Met Ala Trp Ser Phe Arg Ala Lys Val Gln Leu Gly Gly Leu Leu Leu
1               5                   10                  15

Ser Leu Leu Gly Trp Val Cys Ser Cys Val Thr Thr Ile Leu Pro Gln
            20                  25                  30

Trp Lys Thr Leu Asn Leu Glu Leu Asn Glu Met Glu Thr Trp Ile Met
        35                  40                  45

Gly Ile Trp Glu Val Cys Val Asp Arg Glu Glu Val Ala Thr Val Cys
    50                  55                  60

Lys Ala Phe Glu Ser Phe Leu Ser Leu Pro Gln Glu Leu Gln Val Ala
65                  70                  75                  80

Arg Ile Leu Met Val Ala Ser His Gly Leu Gly Leu Leu Gly Leu Leu
                85                  90                  95

Leu Cys Ser Phe Gly Ser Glu Cys Phe Gln Phe His Arg Ile Arg Trp
            100                 105                 110

Val Phe Lys Arg Arg Leu Gly Leu Leu Gly Arg Thr Leu Glu Ala Ser
        115                 120                 125

Ala Ser Ala Thr Thr Leu Leu Pro Val Ser Trp Val Ala His Ala Thr
    130                 135                 140

Ile Gln Asp Phe Trp Asp Asp Ser Ile Pro Asp Ile Pro Arg Trp
145                 150                 155                 160

Glu Phe Gly Gly Ala Leu Tyr Leu Gly Trp Ala Ala Gly Ile Phe Leu
                165                 170                 175

Ala Leu Gly Gly Leu Leu Ile Phe Ser Ala Cys Leu Gly Lys Glu
            180                 185                 190

Asp Val Pro Phe Pro Leu Met Ala Gly Pro Thr Val Pro Leu Ser Cys
        195                 200                 205

Ala Pro Val Glu Glu Ser Asp Gly Ser Phe His Leu Met Leu Arg Pro
    210                 215                 220

Arg Asn Leu Val Ile
225
```

<210> SEQ ID NO 12
<211> LENGTH: 211
<212> TYPE: PRT
<213> ORGANISM: Homo sapiens

<400> SEQUENCE: 12

```
Met Ala Asn Ala Gly Leu Gln Leu Leu Gly Phe Ile Leu Ala Phe Leu
1               5                   10                  15

Gly Trp Ile Gly Ala Ile Val Ser Thr Ala Leu Pro Gln Trp Arg Ile
            20                  25                  30

Tyr Ser Tyr Ala Gly Asp Asn Ile Val Thr Ala Gln Ala Met Tyr Glu
        35                  40                  45

Gly Leu Trp Met Ser Cys Val Ser Gln Ser Thr Gly Gln Ile Gln Cys
    50                  55                  60

Lys Val Phe Asp Ser Leu Leu Asn Leu Ser Ser Thr Leu Gln Ala Thr
65                  70                  75                  80

Arg Ala Leu Met Val Val Gly Ile Leu Leu Gly Val Ile Ala Ile Phe
                85                  90                  95
```

```
Val Ala Thr Val Gly Met Lys Cys Met Lys Cys Leu Glu Asp Asp Glu
            100                 105                 110

Val Gln Lys Met Arg Met Ala Val Ile Gly Gly Ala Ile Phe Leu Leu
            115                 120                 125

Ala Gly Leu Ala Ile Leu Val Ala Thr Ala Trp Tyr Gly Asn Arg Ile
            130                 135                 140

Val Gln Glu Phe Tyr Asp Pro Met Thr Pro Val Asn Ala Arg Tyr Glu
145                 150                 155                 160

Phe Gly Gln Ala Leu Phe Thr Gly Trp Ala Ala Ser Leu Cys Leu
                    165                 170                 175

Leu Gly Gly Ala Leu Leu Cys Cys Ser Cys Pro Arg Lys Thr Thr Ser
            180                 185                 190

Tyr Pro Thr Pro Arg Pro Tyr Pro Lys Pro Ala Pro Ser Ser Gly Lys
            195                 200                 205

Asp Tyr Val
    210

<210> SEQ ID NO 13
<211> LENGTH: 211
<212> TYPE: PRT
<213> ORGANISM: Homo Sapiens

<400> SEQUENCE: 13

Met Ala Asn Ser Gly Leu Gln Leu Leu Gly Phe Ser Met Ala Leu Leu
1               5                   10                  15

Gly Trp Val Gly Leu Val Ala Cys Thr Ala Ile Pro Gln Trp Gln Met
            20                  25                  30

Ser Ser Tyr Ala Gly Asp Asn Ile Ile Thr Ala Gln Ala Met Tyr Lys
            35                  40                  45

Gly Leu Trp Met Asp Cys Val Thr Gln Ser Thr Gly Met Met Ser Cys
    50                  55                  60

Lys Met Tyr Asp Ser Val Leu Ala Leu Ser Ala Ala Leu Gln Ala Thr
65                  70                  75                  80

Arg Ala Leu Met Val Val Ser Leu Val Leu Gly Phe Leu Ala Met Phe
                85                  90                  95

Val Ala Thr Met Gly Met Lys Cys Thr Arg Cys Gly Gly Asp Asp Lys
            100                 105                 110

Val Lys Lys Ala Arg Ile Ala Met Gly Gly Ile Ile Phe Ile Val
            115                 120                 125

Ala Gly Leu Ala Ala Leu Val Ala Cys Ser Trp Tyr Gly His Gln Ile
            130                 135                 140

Val Thr Asp Phe Tyr Asn Pro Leu Ile Pro Thr Asn Ile Lys Tyr Glu
145                 150                 155                 160

Phe Gly Pro Ala Ile Phe Ile Gly Trp Ala Gly Ser Ala Leu Val Ile
                    165                 170                 175

Leu Gly Gly Ala Leu Leu Ser Cys Ser Cys Pro Gly Asn Glu Ser Lys
            180                 185                 190

Ala Gly Tyr Arg Ala Pro Arg Ser Tyr Pro Lys Ser Asn Ser Ser Lys
            195                 200                 205

Glu Tyr Val
    210
```

CLAUDIN POLYPEPTIDES

This application is a national-stage application under 35 U.S.C. § 371 of international application PCT/US 01/25662, filed on Aug. 15, 2001 designating the United States and published in English on Feb. 21, 2002; which claims the benefit under 35 U.S.C. 119(e) of U.S. provisional applications Ser. No. 60/225,513, filed Aug. 15, 2000; and Ser. No. 60/225,794, filed Aug. 15, 2000; all of which are incorporated by reference herein.

FIELD OF THE INVENTION

This invention relates to novel human and murine polypeptides of the Claudin polypeptide family, and to methods of making and using them.

BACKGROUND OF THE INVENTION

The Claudin polypeptides are a related group of "tetraspan" polypeptides, polypeptides having four membrane-spanning or transmembrane domains, that are associated with cellular tight junctions. Tight junctions, which are also called "zona occludens", form a regulated, semipermeable barrier in the intercellular spaces within sheets of epithelial or endothelial cells. Inadequate or improperly regulated epithelial or endothelial barrier function contributes to the initiation, maintenance, and exacerbation of inflammation in tissues such as the gut, lungs, etc. Tight junctions also form a "fence" separating the apical and basolateral regions of these cells' membranes, allowing the establishment of different physiological environments on the opposite sides of a cell sheet, such as the different physiological environments required for transport of materials across the intestinal epithelium. It has also been proposed that tight junctions contain aqueous pores, with paracellular transport between the cells of an epithelial or endothelial sheet occurring through these pores. Claudin family polypeptides are expressed in epithelial cells and/or endothelial cells throughout development, with individual members of the Claudin polypeptide family being expressed in different tissues. The physiological functions associated with a particular Claudin polypeptide are related to the functions performed by the particular tissue(s) in which it is expressed.

Common structural features of the Claudin family of polypeptides are the four membrane-spanning (transmembrane) domains, the two extracellular loops formed by the transmembrane domains, and the cytoplasmic tail domain. The cytoplasmic tail domain is thought to be involved in interactions with other tight-junction-associated proteins such as the ZO (zona occludens) family of proteins. These interactive activities of Claudin polypeptides are thought to involve PDZ-domain-containing polypeptides, with a PDZ domain binding to the C-terminal residues of the cytoplasmic tail domain of a Claudin polypeptide; association of PDZ-containing polypeptides may then result in oligomerization of Claudin polypeptides. The extracellular loop domains of Claudin polypeptides may contribute to tight junction formation, which is an important aspect of both the barrier function and the ion transport function of Claudin polypeptides, and/or act as a receptor for viral proteins, enterotoxins, or allergens. The tight junction formation activities of the Claudin polypeptide family are believed to occur through homotypic interactions with the extracellular loops of the same Claudin polypeptide expressed on neighboring epithelial or endothelial cells, or heterotypic interactions with the extracellular loops of other Claudin family members or other non-Claudin polypeptides. In addition, there is evidence that the biological effects of Claudin polypeptides involve a requirement for Claudin polypeptides, and particularly their most N-terminal extracellular domain, in the processing of matrix metalloproteinases to their active form (Miyamori et al., 2001, *J Biol Chem* 276: 2804–28211). Because of their roles in tight junction formation, epithelial and endothelial barrier function, ion transport, and viral protein, enterotoxin, or allergen binding, Claudin polypeptides are associated with conditions involving unregulated or improperly regulated transport across the epithelium or endothelium such as inflammation, asthma, allergy, metastasis of cancer cells, and ion transport disorders such as magnesium transport defects in the kidney. In addition, because a Claudin polypeptide expressed in neural cells has been shown to be required for formation of the myelin sheath in oligodendrocytes, Claudin polypeptides are associated with demyelination conditions such as multiple sclerosis (MS), autoimmune encephalomyelitis, optic neuritis, progressive multifocal leukoencephalopathy (PML), etc.

Characteristics and activities of the Claudin polypeptide family are described further in the following references: Fujitaab K et al., 2000, Clostridium perfringens enterotoxin binds to the second extracellular loop of claudin-3, a tight junction integral membrane protein, FEBS Lett. 476: 258–261; Kinugasa T et al., 2000, Claudins regulate the intestinal barrier in response to immune mediators, Gastroenterology 118: 1001–1011; Tsukita S and Furuse M, 2000, Pores in the wall: claudins constitute tight junction strands containing aqueous pores, J Cell Biol. 149: 13–16; Bronstein J M et al., 2000, Involvement of OSP/claudin-11 in oligodendrocyte membrane interactions: role in biology and disease, J Neurosci Res. 59: 706–711; Itoh M et al., 1999, Direct binding of three tight junction-associated MAGUKs, ZO-1, ZO-2, and ZO-3, with the COOH termini of claudins, J Cell Biol. 147: 1351–1363; Furuse M et al., 1999, Manner of interaction of heterogeneous claudin species within and between tight junction strands, J Cell Biol. 147: 891–903; Morita K et al., 1999, Endothelial claudin: claudin-5/TM-VCF constitutes tight junction strands in endothelial cells, J Cell Biol. 147: 185–194; Kubota K et al., 1999, Ca(2+)-independent cell-adhesion activity of claudins, a family of integral membrane proteins localized at tight junctions, Curr Biol. 9: 1035–1038; Wan H et al., 1999, Der p 1 facilitates transepithelial allergen delivery by disruption of tight junctions, J Clin Invest 104: 123–133; Simon D B et al., 1999, Paracellin-1, a renal tight junction protein required for paracellular Mg2+ resorption, Science 285: 103–106; Morita K et al., 1999, Claudin multigene family encoding four-transmembrane domain protein components of tight junction strands, Proc Natl Acad Sci USA. 96: 511–516; Furuse M et al., 1998, A single gene product, claudin-1 or -2, reconstitutes tight junction strands and recruits occludin in fibroblasts, J Cell Biol. 143: 391–401; Furuse M et al., 1998, Claudin-1 and -2: novel integral membrane proteins localizing at tight junctions with no sequence similarity to occludin, J Cell Biol. 141: 1539–1550; all of which are incorporated by reference herein.

In order to develop more effective treatments for conditions involving disruption of epithelial or endothelial barrier function or unregulated transport across the epithelium or endothelium, such as inflammatory bowel disease, or involving demyelination, such as multiple sclerosis, information is needed about previously unidentified members of the Claudin polypeptide family, so that the characteristics and activities of such new Claudin family members can be ascertained. In particular, there is a need for characterization of previously unidentified human Claudin polypeptides.

SUMMARY OF THE INVENTION

The present invention is based upon the discovery of a new member of the human Claudin polypeptide family, human Claudin-21.

The invention provides an isolated polypeptide comprising an amino acid sequence selected from the group consisting of:

(a) an amino acid sequence selected from the group consisting of SEQ ID NO:4 and amino acids 1 to 13 of SEQ ID NO:4;
(b) SEQ ID NO:6;
(c) an amino acid sequence selected from the group consisting of amino acids 1 to 10 of SEQ ID NO:6, amino acids 1 to 33 of SEQ ID NO:6, amino acids 11 to 30 of SEQ ID NO:6, amino acids 12 to 26 of SEQ ID NO:6, amino acids 25 to 220 of SEQ ID NO:6, amino acids 34 to 81 of SEQ ID NO:6, amino acids 82 to 101 of SEQ ID NO:6, amino acids 82 to 102 of SEQ ID NO:6, amino acids 103 to 116 of SEQ ID NO:6, amino acids 117 to 145 of SEQ ID NO:6, amino acids 118 to 137 of SEQ ID NO:6, amino acids 146 to 161 of SEQ ID NO:6, amino acids 162 to 181 of SEQ ID NO:6, amino acids 162 to 191 of SEQ ID NO:6, and amino acids 192 to 220 of SEQ ID NO:6;
(d) fragments of the amino acid sequences of any of (a)–(c) comprising at least 20 contiguous amino acids;
(e) fragments of the amino acid sequences of any of (a)–(c) comprising at least 30 contiguous amino acids;
(f) fragments of the amino acid sequences of any of (a)–(c) having Claudin polypeptide activity;
(g) fragments of the amino acid sequences of any of (a)–(c) comprising extracellular loop domain amino acid sequences;
(h) fragments of the amino acid sequences of any of (a)–(c) comprising cytoplasmic tail domain amino acid sequences;
(i) amino acid sequences comprising at least 20 amino acids and sharing amino acid identity with the amino acid sequences of any of (a)–(h), wherein the percent amino acid identity is selected from the group consisting of: at least 70%, at least 75%, at least 80%, at least 85%, at least 90%, at least 95%, at least 97.5%, at least 99%, and at least 99.5%;
(j) an amino acid sequence of (i), wherein a polypeptide comprising said amino acid sequence of (i) binds to an antibody that also binds to a polypeptide comprising an amino acid sequence of any of (a)–(h); and
(k) an amino acid sequence of (i) or (j) having Claudin polypeptide activity.

The invention further provides an isolated polypeptide comprising an amino acid sequence selected from the group consisting of:

(a) an amino acid sequence selected from the group consisting of SEQ ID NO:10 and amino acids 19 through 33 of SEQ ID NO:10;
(b) SEQ ID NO:8;
(c) an amino acid sequence selected from the group consisting of amino acids 5 through 27 of SEQ ID NO:8; amino acids 28 through 76 of SEQ ID NO:8; amino acids 77 through 99 of SEQ ID NO:8; amino acids 100 through 118 of SEQ ID NO:8; amino acids 119 through 141 of SEQ ID NO:8; amino acids 142 through 160 of SEQ ID NO:8; amino acids 161 through 183 of SEQ ID NO:8; and amino acids 184 through 211 of SEQ ID NO:8;
(d) fragments of the amino acid sequences of any of (a)–(c) comprising at least 20 contiguous amino acids;
(e) fragments of the amino acid sequences of any of (a)–(c) comprising at least 30 contiguous amino acids;
(f) fragments of the amino acid sequences of any of (a)–(c) having Claudin polypeptide activity;
(g) fragments of the amino acid sequences of any of (a)–(c) comprising extracellular loop domain amino acid sequences;
(h) fragments of the amino acid sequences of any of (a)–(c) comprising cytoplasmic tail domain amino acid sequences;
(i) amino acid sequences comprising at least 20 amino acids and sharing amino acid identity with the amino acid sequences of any of (a)–(h), wherein the percent amino acid identity is selected from the group consisting of: at least 70%, at least 75%, at least 80%, at least 85%, at least 90%, at least 95%, at least 97.5%, at least 99%, and at least 99.5%;
(j) an amino acid sequence of (i), wherein a polypeptide comprising said amino acid sequence of (i) binds to an antibody that also binds to a polypeptide comprising an amino acid sequence of any of (a)–(h); and
(k) an amino acid sequence of (i) or (j) having Claudin polypeptide activity.

Also provided by the invention is an isolated polypeptide comprising an amino acid sequence selected from the group consisting of:

(a) SEQ ID NO:11;
(b) an amino acid sequence selected from the group consisting of amino acids 11 through 33 of SEQ ID NO:11; amino acids 77 through 99 of SEQ ID NO:11; amino acids 119 through 141 of SEQ ID NO:11; and amino acids 167 through 189 of SEQ ID NO:11;
(c) an amino acid sequence selected from the group consisting of amino acids 34 through 76 of SEQ ID NO:11; amino acids 100 through 118 of SEQ ID NO:11; amino acids 142 through 166 of SEQ ID NO:11; and amino acids 190 through 229 of SEQ ID NO:11;
(d) fragments of the amino acid sequences of any of (a)–(c) comprising at least 20 contiguous amino acids;
(e) fragments of the amino acid sequences of any of (a)–(c) comprising at least 30 contiguous amino acids;
(f) fragments of the amino acid sequences of any of (a)–(c) having Claudin polypeptide activity;
(g) fragments of the amino acid sequences of any of (a)–(c) comprising extracellular loop domain amino acid sequences;
(h) fragments of the amino acid sequences of any of (a)–(c) comprising cytoplasmic tail domain amino acid sequences;
(i) amino acid sequences comprising at least 20 amino acids and sharing amino acid identity with the amino acid sequences of any of (a)–(h), wherein the percent amino acid identity is selected from the group consisting of: at least 70%, at least 75%, at least 80%, at least 85%, at least 90%, at least 95%, at least 97.5%, at least 99%, and at least 99.5%;
(j) an amino acid sequence of (i), wherein a polypeptide comprising said amino acid sequence of (i) binds to an antibody that also binds to a polypeptide comprising an amino acid sequence of any of (a)–(h); and (k) an amino acid sequence of (i) or (j) having Claudin polypeptide activity.

Other aspects of the invention are isolated nucleic acids encoding polypeptides of the invention, and isolated nucleic acids, preferably having a length of at least 15 nucleotides, that hybridize under conditions of moderate stringency to the nucleic acids encoding polypeptides of the invention. In preferred embodiments of the invention, such nucleic acids encode a polypeptide having Claudin polypeptide activity, or comprise a nucleotide sequence that shares nucleotide sequence identity with the nucleotide sequences of the nucleic acids of the invention, wherein the percent nucleotide sequence identity is selected from the group consisting of: at least 70%, at least 75%, at least 80%, at least 85%, at least 90%, at least 95%, at least 97.5%, at least 99%, and at least 99.5%;

Also encompassed by the present invention are isolated polypeptides and nucleic acids consisting of amino acid sequences and nucleotide sequences, respectively, disclosed herein.

Further provided by the invention are expression vectors and recombinant host cells comprising at least one nucleic acid of the invention, and preferred recombinant host cells wherein said nucleic acid is integrated into the host cell genome.

Also provided is a process for producing a polypeptide encoded by the nucleic acids of the invention, comprising culturing a recombinant host cell under conditions promoting expression of said polypeptide, wherein the recombinant host cell comprises at least one nucleic acid of the invention. A preferred process provided by the invention further comprises purifying said polypeptide. In another aspect of the invention, the polypeptide produced by said process is provided.

Further aspects of the invention are isolated antibodies that bind to the polypeptides of the invention, preferably monoclonal antibodies, also preferably humanized antibodies or humanized antibodies, and preferably wherein the antibody inhibits the activity of said polypeptides.

The invention additionally provides a method of designing an inhibitor of the polypeptides of the invention, the method comprising the steps of determining the three-dimensional structure of any such polypeptide, analyzing the three-dimensional structure for the likely binding sites of substrates, synthesizing a molecule that incorporates a predicted reactive site, and determining the polypeptide-inhibiting activity of the molecule.

In a further aspect of the invention, a method is provided for identifying compounds that alter Claudin polypeptide activity comprising
  (a) mixing a test compound with a polypeptide of the invention; and
  (b) determining whether the test compound alters the Claudin polypeptide activity of said polypeptide.

In another aspect of the invention, a method is provided identifying compounds that inhibit the binding activity of Claudin polypeptide polypeptides comprising
  (a) mixing a test compound with a polypeptide of the invention and a binding partner of said polypeptide; and
  (b) determining whether the test compound inhibits the binding activity of said polypeptide.

The invention also provides a method for increasing tight junction formation or promoting epithelial or endothelial barrier function activities, comprising providing at least one polypeptide of the invention; with a preferred embodiment of the method further comprising increasing said activities in a patient by administering at least one polypeptide of the invention.

Further provided by the invention is a method for decreasing tight junction formation activity or epithelial or endothelial barrier function activity, comprising providing at least one antagonist of the polypeptides of the invention; with a preferred embodiment of the method further comprising decreasing said activities in a patient by administering at least one antagonist of the polypeptides of the invention, and with a further preferred embodiment wherein the antagonist is an antibody that inhibits the activity of any of said polypeptides.

The invention additionally provides a method for treating an epithelial or endothelial barrier function condition comprising administering the polypeptide of the invention; with a preferred embodiment wherein the epithelial or endothelial barrier function condition is selected from the group consisting of inflammatory bowel disease, asthma, allergy, and ion transport defects.

The invention additionally provides a method for treating a demyelination condition comprising administering the polypeptide of the invention; with a preferred embodiment wherein the demyelination condition is selected from the group consisting of multiple sclerosis, autoimmune encephalomyelitis, optic neuritis, and progressive multifocal leukoencephalopathy.

In other aspects of the invention, a method is provided for treating a viral or enterotoxic condition comprising administering an antagonist of the polypeptide of the invention; with a preferred embodiment wherein the viral or enterotoxic condition is exposure to Clostridium perfringens enterotoxin, and with an additional preferred embodiment in which the antagonist blocks binding of Clostridium perfringens enterotoxin to the extracellular loops of a Claudin polypeptide of the invention.

DETAILED DESCRIPTION OF THE INVENTION

Structure of Human Claudin Polypeptides

We have identified a new members of the Claudin polypeptide family, human Claudin-21, human Claudin-19, and human Claudin-22. Typical structural elements common to members of the Claudin polypeptide family include a non-cleaved signal peptide sequence, four membrane-spanning domains, two extracellular loops formed by the membrane-spanning domains, and a cytoplasmic tail at the C-terminus of the polypeptide. Both the N-terminus and the C-terminus of the polypeptide are intracellular. The two extracellular loop domains of Claudin polypeptides are located between the first and second transmembrane domains and between the third and fourth transmembrane domains of the polypeptide, respectively. The short region between the second and third transmembrane domains of the polypeptide is intracellular. The cytoplasmic tail domain of Claudin polypeptides extends from the fourth transmembrane domain to the C-terminus of the polypeptide.

The amino acid sequences of human Claudin-21 (SEQ ID NO:6), human Claudin-19 (SEQ ID NO:8), and human Claudin-22 (SEQ ID NO:11) contain the structural features of Claudin polypeptides. Human Claudin-21 contains a signal sequence domain (amino acids 12 to 26 of SEQ ID NO:6) that would direct cleavage of the full-length SEQ ID NO:6 amino acid sequence between amino acids 24 and 25 of SEQ ID NO:6 to form a mature or processed Claudin-21 polypeptide with amino acid 25 of SEQ ID NO:6 as the N-terminal amino acid. However, this signal sequence domain is also predicted to be located within the first transmembrane (TM) domain, which comprises amino acids 11 to 30 of SEQ ID NO:6, consistent with the other Claudin family members in which the signal sequence is not cleaved but is inserted into the cell membrane with the very N-terminal end of the Claudin polypeptide (in this case, amino acids 1 to 10 of SEQ ID NO:6) located inside the cell. Human Claudin-21 is also predicted to have a second TM domain comprising amino acids 82 to 101 of SEQ ID NO:6, a third TM domain comprising amino acids 118 to 137 of SEQ ID NO:6, and a fourth TM domain comprising amino acids 162 to 181 of SEQ ID NO:6. Hidden Markov Model (HMM) analysis predicts the same non-cleaved signal and similar transmembrane domains: amino acids 12 through 31 of SEQ ID NO:6; amino acids 82 through 105 of SEQ ID NO:6; amino acids 118 through 140 of SEQ ID NO:6; and amino acids 166 through 188 of SEQ ID NO:6. These predicted locations for the human Claudin-21 TM domains also correspond well with those identified by Morita et al. (1999, Claudin multigene family encoding four-transmembrane domain protein components of tight junction strands, Proc Natl Acad Sci USA. 96: 511–516) for other members of the Claudin polypeptide family. Based on the alignments with other family members and by reference to FIG. 1 of Morita et al., the four transmembrane domains are predicted to extend from amino acids 1 to 33, 82 to 102, 117 to 145, and 162 to 191 of SEQ ID NO:6, respectively. These predicted locations for the four TM domains of human Claudin-21 places the first extracellular loop of human Claudin-21 as beginning approximately around amino acid 31 to amino acid 34 of SEQ ID NO:6 and extending to approximately amino acid 81 of SEQ ID NO:6, and preferably from amino acid 34 to amino acid 81 of SEQ ID NO:6, and the second extracellular loop of human Claudin-21 as beginning approximately around amino acid 138 to amino acid 146 of SEQ ID NO:6 and extending to approximately amino acid 161 of SEQ ID NO:6, and preferably from amino acid 146 to amino acid 161 of SEQ ID NO:6. The intracellular sequence between the second and third TM domains extends from approximately amino acid 102 or 103 of SEQ ID NO:6 to approximately amino acid 116 to 117 of SEQ ID NO:6, and preferably from amino acid 103 to amino acid 116 of SEQ ID NO:6. The cytoplasmic tail domain of human Claudin-21 begins approximately around amino acid 182 to amino acid 192 of SEQ ID NO:6 and extends to the predicted C-terminus of SEQ ID NO:6 at amino acid 220; preferably, the cytoplasmic tail domain of SEQ ID NO:6 extends from amino acid 192 to amino acid 220 of SEQ ID NO:6. Human Claudin-19 contains a non-cleaved signal sequence domain (amino acids 8 through 25 of SEQ ID NO:8) that would direct cleavage of the full-length SEQ ID NO:8 amino acid sequence between amino acids 24 and 25 of SEQ ID NO:8. Hidden Markov Model (HMM) analysis predicts the following transmembrane domains for Human Claudin-19: amino acids 5 through 27 of SEQ ID NO:8; amino acids 77 through 99 of SEQ ID NO:8; amino acids 119 through 141 of SEQ ID NO:8; and amino acids 161 through 183 of SEQ ID NO:8. Human Claudin-22 contains a non-cleaved signal sequence domain (amino acids 11 through 27 of SEQ ID NO:11) that would direct cleavage of the full-length SEQ ID NO:11 amino acid sequence between amino acids 24 and 25 of SEQ ID NO:11. Hidden Markov Model (HMM) analysis predicts the following transmembrane domains for Human Claudin-22: amino acids 11 through 33 of SEQ ID NO:11; amino acids 77 through 99 of SEQ ID NO:11; amino acids 119 through 141 of SEQ ID NO:11; and amino acids 167 through 189 of SEQ ID NO:11. The skilled artisan will recognize that the boundaries of these regions of these polypeptides are approximate and that the precise boundaries of such domains, as for example the boundaries of the transmembrane domains, may differ from those predicted herein for human Claudin-19, -21, and -22.

The most C-terminal residues of the cytoplasmic tail domains of Claudin polypeptides are believed to be involved with interaction with PDZ-domain-containing proteins, such that substitutions of those residues are likely be associated with an altered PDZ domain recognition pattern or binding function, or with a lack of that function, for the polypeptide. Most members of the Claudin polypeptide family, such as human Claudin-19 described herein, have a -Tyr-Val-COOH amino acid sequence at their C-termini. Human Claudin-21 is predicted to have an -Asp-Pro-Gln-Val-COOH (SEQ ID NO:14) amino acid sequence at its C-terminus. Although this does not match exactly the C-terminal amino acid sequences of other Claudin family polypeptides, it is consistent in most respects with the consensus requirements for "Group 1" polypeptides that interact with PDZ domains (Cowburn D, 1997, *Curr Opin Struct Bid* 7: 835–838; which is incorporated by reference herein): Val/Ile/Leu/Met as the C-terminal residue, with preference for Thr/Ser/Tyr at the -2 position and Glu at the -3 position. Human Claudin-21 has Val as the C-terminal residue and Asp, having an acidic side chain like Glu, at the -3 position. Human Claudin-22 has Ile as the C-terminal residue. Therefore, human Claudin-21 and -22 are predicted to interact with PDZ-domain-containing polypeptides, although they may interact with different subsets of PDZ domains than other Claudin family members, or they may exhibit different kinetics or affinity in their interactions with PDZ-domain-containing polypeptides.

Biological Activities and Functions of Claudin Polypeptides of the Invention

As used herein, "Claudin polypeptides of the invention" includes human Claudin-19, human Claudin-21, human Claudin-22, and as applicable, species homologues such as murine Claudin-19 (SEQ ID NO:9) and murine Claudin-21 (SEQ ID NO:7), and variants and fragments of these human Claudin polypeptides and their species homologues. Claudin polypeptides of the invention have biological activities and functions that are consistent with those of the other Claudin family polypeptides. Polypeptides of the Claudin family are expressed in cell types including epithelial and endothelial cells throughout development. Typical biological activities or functions associated with this family of polypeptides are tight junction formation, epithelial or endothelial barrier function, ion transport, viral protein binding, homotypic or heterotypic binding, and binding PDZ domain binding. Polypeptides having tight junction formation activity bind to other tight-junction-associated molecules to form tight junction structures which regulate epithelial or endothelial barrier function and paracellular transport. The tight junction formation activity is associated with the extracellular loops and possibly with the cytoplasmic tail domain of Claudin polypeptides. Thus, for uses requiring tight junction formation activity, preferred human Claudin-19, -21, and -22 polypeptides include those having the extracellular loop domains and exhibiting tight junction formation activities such as epithelial or endothelial barrier function, paracellular ion transport, or viral protein binding. Preferred Claudin polypeptides of the invention further include oligomers or fusion polypeptides comprising at least one extracellular loop or cytoplasmic tail domain of one or more Claudin polypeptides of the invention, and fragments of any of these polypeptides that have tight junction formation activity. The tight junction formation activity of human Claudin-19, -21, and -22 and other Claudin family polypeptides may be determined, for example, by introducing Claudin polypeptides into cells that do not normally form tight junctions, such a L fibroblasts, along with occludin or any other polypeptide that the Claudin polypeptide needs to interact with in the formation of tight junctions, then visualizing the resulting tight junction structures by electron microscopy or immunofluorescence methods (see for example Furuse M et al., 1998, A single gene product, claudin-1 or -2, reconstitutes tight junction strands and recruits occludin in fibroblasts, J Cell Biol. 143: 391–401). Alternatively, the paracellular ion transport activity of human Claudin-19, -21, and -22 and other Claudin family polypeptides may be assayed by electrophysiology or through the use of luminescent ion indicator molecules such as aequorin, preferably in micellular preparations from cells expressing Claudin polypeptides.

Claudin polypeptides such as human Claudin-19, -21, and -22 have homotypic binding, heterotypic binding, viral protein binding, and/or enterotoxin binding activity; each of these binding activities is associated with the extracellular loop domains of Claudin polypeptides. Thus, for uses requiring homotypic binding, heterotypic binding, viral protein binding, and/or enterotoxin binding activity, preferred Claudin polypeptides of the invention include those having at least one extracellular loop domain and exhibiting at least one such binding activity. Claudin polypeptides also have PDZ domain binding activity associated with the cytoplasmic tail domains of Claudin polypeptides. Thus, for uses requiring PDZ domain binding activity, preferred Claudin polypeptides of the invention include those having a cytoplasmic tail domain and exhibiting PDZ domain binding activity. Preferred Claudin polypeptides of the invention further include oligomers or fusion polypeptides comprising at least one extracellular loop domain and/or cytoplasmic tail domain of one or more Claudin polypeptides of the invention, and fragments of any of these polypeptides that have homotypic binding, heterotypic binding, viral protein binding, enterotoxin binding, and/or PDZ domain binding activity. The binding activity or activities of human Claudin-19, -21, and -22 and other Claudin family polypeptides may be determined, for example, in a yeast two-hybrid assay, or in an in vitro assay that measures binding between a Claudin polypeptide and one of its homotypic, heterotypic, viral protein, enterotoxin, and/or PDZ-domain-containing binding partners, where either the Claudin polypeptide or its binding partner is labeled with a radioactive, fluorescent, or bioluminescent protein such that binding can be detected.

The term "human Claudin polypeptide activity," as used herein, includes any one or more of the following: tight junction formation, epithelial or endothelial barrier function, and ion transport activity; homotypic binding, heterotypic binding, viral protein binding, enterotoxin binding, and PDZ domain binding activity; as well as the ex vivo and in vivo activities of Claudin polypeptides of the invention. The degree to which Claudin polypeptides of the invention and fragments and other derivatives of these polypeptides exhibit these activities can be determined by standard assay methods. Exemplary assays are disclosed herein; those of skill in the art will appreciate that other, similar types of assays can be used to measure the biological activities of Claudin polypeptides of the invention and other Claudin family members.

One aspect of the biological activity of Claudin polypeptides including human Claudin-19, -21, and -22 is the ability of members of this polypeptide family to bind particular binding partners such homotypic and heterotypic polypeptides, viral proteins, enterotoxins, and PDZ-domain-containing polypeptides, with the extracellular loop domains binding, for example, to homotypic polypeptides, and the cytoplasmic tail domain binding to PDZ-domain-containing polypeptides. The term "binding partner," as used herein, includes ligands, receptors, substrates, antibodies, other Claudin polypeptides, the same human Claudin-19, -21, or -22 polypeptide (in the case of homotypic interactions), and any other molecule that interacts with a human Claudin-19, -21, or -22 polypeptide through contact or proximity between particular portions of the binding partner and the human Claudin-19, -21, or -22 polypeptide. Binding partners for Claudin polypeptides of the invention are also expressed by epithelial and endothelial cells, as Claudin polypeptides expressed in epithelial cells bind to molecules on neighboring epithelial cells to form tight junctions, and Claudin polypeptides expressed in endothelial cells bind to molecules on neighboring endothelial cells. Therefore, the interactions between Claudin polypeptides of the invention and their binding partners are likely involved in mediating interactions between adjacent epithelial cells, and interactions between adjacent endothelial cells. Because the extracellular loop domains of Claudin polypeptides of the invention bind to homotypic or heterotypic polypeptides, a derivative polypeptide comprising one or more extracellular loop domains when expressed as a separate fragment from the rest of a human Claudin-19, -21, or -22 polypeptide, or as a soluble polypeptide, fused for example to an immunoglobulin Fc domain, is expected to disrupt the binding of Claudin polypeptides of the invention to its binding partners. By binding to one or more binding partners, the separate extracellular loop domain(s) polypeptide likely prevents binding by the native human Claudin-19, -21, and -22 polypeptide(s), and so acts in a dominant negative fashion to inhibit the biological activities mediated via binding of Claudin polypeptides of the invention to homotypic or heterotypic polypeptides. The biological activities and partner-binding properties of human Claudin-19, -21, and -22 and other Claudin family polypeptides may be assayed by standard methods and by those assays described herein.

Polypeptides of the Claudin family such as human Claudin-19, -21, and -22 are involved in epithelial or endothelial barrier function and transport diseases or conditions, that share as a common feature abnormal tight junction formation or improperly regulated tight junction function (i.e. abnormal epithelial or endothelial barrier function) in their etiology. More specifically, the following conditions involving epithelial or endothelial barrier function and/or binding to Claudin polypeptides are those that are known or are likely to involve the biological activities of Claudin polypeptides: inflammation, asthma, allergy, metastasis of cancer cells, ion transport disorders such as magnesium transport defects in the kidney, inflammatory bowel disease, and exposure to Clostridium perfringens enterotoxin (CPE). In addition, because a Claudin polypeptide expressed in neural cells has been shown to be required for formation of the myelin sheath in oligodendrocytes, Claudin polypeptides are associated with demyelination conditions such as multiple sclerosis (MS), autoimmune encephalomyelitis, optic neuritis, and progressive multifocal leukoencephalopathy (PML). Also, diseases that are promoted by one or more of the conditions above may involve Claudin polypeptides, directly or indirectly. For example, susceptibility to sudden infant death syndrome (SIDS) has been associated with exposure to CPE. Blocking or inhibiting the interactions between Claudin polypeptides of the invention and their substrates, ligands, receptors, binding partners, and or other interacting polypeptides is an aspect of the invention and provides methods for treating or ameliorating these diseases and conditions through the use of inhibitors of human Claudin-19, -21, and -22 activity. Examples of such inhibitors or antagonists are described in more detail below. For certain conditions involving a defect in epithelial or endothelial barrier function or ion transport associated with too little human Claudin-19, -21, and -22 activity, methods of treating or ameliorating these conditions comprise increasing the amount or activity of Claudin polypeptides of the invention by providing isolated Claudin polypeptides of the invention or active fragments or fusion polypeptides thereof, or by providing compounds (agonists) that activate endogenous or exogenous Claudin polypeptides of the invention. Additional uses for Claudin polypeptides of the invention and agonists and antagonists thereof include diagnostic reagents for epithelial or endothelial transport diseases; research reagents for investigation of occludin or ZO family polypeptides and the formation of tight junctions; purification, processing, and preservation of occludin or ZO polypeptides or of epithelial or endothelial cells; or as a carrier or targeting molecule for the delivery of therapeutic agents, particularly in view of the role of Claudins in the tight junctions of the blood-brain barrier (Kniesel U and Wolburg H, 2000, Cell Mol Neurobiol. 20: 57–76, which is incorporated by reference herein).

Claudin Polypeptides of the Invention

A human Claudin-19, -21, or -22 polypeptide is a polypeptide that shares a sufficient degree of amino acid identity or similarity to human Claudin-19, -21, or -22 polypeptide amino acid sequence such as those shown in Table 1 to (A) be identified by those of skill in the art as a polypeptide likely to share particular structural domains and/or (B) have biological activities in common with human Claudin polypeptides and/or (C) bind to antibodies that also specifically bind to other human Claudin polypeptides. Claudin polypeptides of the invention may be isolated from naturally occurring sources, or have the same structure as naturally occurring Claudin polypeptides, or may be produced to have structures that differ from naturally occurring Claudin polypeptides. Polypeptides derived from any human Claudin-19, -21, and -22 polypeptide by any type of alteration (for example, but not limited to, insertions, deletions, or substitutions of amino acids; changes in the state of glycosylation of the polypeptide; refolding or isomerization to change its three-dimensional structure or self-association state; and changes to its association with other polypeptides or molecules) are also Claudin polypeptides of the invention. Therefore, the polypeptides provided by the invention include polypeptides characterized by amino acid sequences similar to those of the Claudin polypeptides of the invention described herein, but into which modifications are naturally provided or deliberately engineered. A polypeptide that shares biological activities in common with Claudin polypeptides of the invention is a polypeptide having human Claudin-19, -21, and -22 activity. Examples of biological activities exhibited by members of the Claudin polypeptide family include, without limitation, tight junction formation, epithelial or endothelial barrier function, ion transport, homotypic or heterotypic binding, viral protein binding, and enterotoxin binding.

The present invention provides both full-length and mature forms of Claudin polypeptides of the invention. Full-length polypeptides are those having the complete primary amino acid sequence of the polypeptide as initially translated. The amino acid sequences of full-length polypeptides can be obtained, for example, by translation of the complete open reading frame ("ORF") of a cDNA molecule. Several full-length polypeptides may be encoded by a single genetic locus if multiple mRNA forms are produced from that locus by alternative splicing or by the use of multiple translation initiation sites. The "mature form" of a polypeptide refers to a polypeptide that has undergone post-translational processing steps such as cleavage of the signal sequence or proteolytic cleavage to remove a prodomain. Multiple mature forms of a particular full-length polypeptide may be produced, for example by cleavage of the signal sequence at multiple sites, or by differential regulation of proteases that cleave the polypeptide. The mature form(s) of such polypeptide may be obtained by expression, in a suitable mammalian cell or other host cell, of a nucleic acid molecule that encodes the full-length polypeptide. The sequence of the mature form of the polypeptide may also be determinable from the amino acid sequence of the full-length form, through identification of signal sequences or protease cleavage sites. The Claudin polypeptides of the invention of the invention also include those that result from post-transcriptional or post-translational processing events such as alternate mRNA processing which can yield a truncated but biologically active polypeptide, for example, a naturally occurring soluble form of the polypeptide. Also encompassed within the invention are variations attributable to proteolysis such as differences in the N- or C-termini upon expression in different types of host cells, due to proteolytic removal of one or more terminal amino acids from the polypeptide (generally from 1 to 5 terminal amino acids).

The invention further includes Claudin polypeptides of the invention with or without associated native-pattern glycosylation. Polypeptides expressed in yeast or mammalian expression systems (e.g., COS-1 or CHO cells) can be similar to or significantly different from a native polypeptide in molecular weight and glycosylation pattern, depending upon the choice of expression system. Expression of polypeptides of the invention in bacterial expression systems, such as E. coli, provides non-glycosylated molecules. Further, a given preparation can include multiple differentially glycosylated species of the polypeptide. Glycosyl groups can be removed through conventional methods, in particular those utilizing glycopeptidase. In general, glycosylated polypeptides of the invention can be incubated with a molar excess of glycopeptidase (Boehringer Mannheim).

Species homologues of Claudin polypeptides of the invention and of nucleic acids encoding them are also provided by the present invention. As used herein, a "species homologue" is a polypeptide or nucleic acid with a different species of origin from that of a given polypeptide or nucleic acid, but with significant sequence similarity to the given polypeptide or nucleic acid, as determined by those of skill in the art. Species homologues may be isolated and identified by making suitable probes or primers from polynucleotides encoding the amino acid sequences provided herein and screening a suitable nucleic acid source from the desired species. The invention also encompasses allelic variants of Claudin polypeptides of the invention and nucleic acids encoding them; that is, naturally-occurring alternative forms of such polypeptides and nucleic acids in which differences in amino acid or nucleotide sequence are attributable to genetic polymorphism (allelic variation among individuals within a population).

Fragments of the Claudin polypeptides of the invention of the present invention are encompassed by the present invention and may be in linear form or cyclized using known methods, for example, as described in H. U. Saragovi, et al., Bio/Technology 10, 773–778 (1992) and in R. S. McDowell, et al., J. Amer. Chem. Soc. 114 9245–9253 (1992), both of which are incorporated by reference herein. Polypeptides and polypeptide fragments of the present invention, and nucleic acids encoding them, include polypeptides and nucleic acids with amino acid or nucleotide sequence lengths that are at least 25% (more preferably at least 50%, or at least 60%, or at least 70%, and most preferably at least 80%) of the length of a human Claudin-19, -21, and -22 polypeptide and have at least 60% sequence identity (more preferably at least 70%, at least 75%, at least 80%, at least 85%, at least 90%, at least 95%, at least 97.5%, or at least 99%, and most preferably at least 99.5%) with that human Claudin-19, -21, and -22 polypeptide or encoding nucleic acid, where sequence identity is determined by comparing the amino acid sequences of the polypeptides when aligned so as to maximize overlap and identity while minimizing sequence gaps. Also included in the present invention are polypeptides and polypeptide fragments, and nucleic acids encoding them, that contain or encode a segment preferably comprising at least 8, or at least 10, or preferably at least 15, or more preferably at least 20, or still more preferably at least 30, or most preferably at least 40 contiguous amino acids. Such polypeptides and polypeptide fragments may also contain a segment that shares at least 70% sequence identity (more preferably at least 70%, at least 75%, at least 80%, at least 85%, at least 90%, at least 95%, at least 97.5%, or at least 99%, and most preferably at least 99.5%) with any such segment of any of the Claudin polypeptides of the invention, where sequence identity is determined by comparing the amino acid sequences of the polypeptides when aligned so as to maximize overlap and identity while minimizing sequence gaps. The percent identity can be determined by visual inspection and mathematical calculation. Alternatively, the percent identity of two amino acid or two nucleic acid sequences can be determined by comparing sequence information using the GAP computer program, version 6.0 described by Devereux et al. (*Nucl. Acids Res.* 12:387, 1984) and available from the University of Wisconsin Genetics Computer Group (UWGCG). The preferred default parameters for the GAP program include: (1) a unary comparison matrix (containing a value of 1 for identities and 0 for non-identities) for nucleotides, and the weighted comparison matrix of Gribskov and Burgess, *Nucl. Acids Res.* 14:6745, 1986, as described by Schwartz and Dayhoff, eds., *Atlas of Polypeptide Sequence and Structure*, National Biomedical Research Foundation, pp. 353–358, 1979; (2) a penalty of 3.0 for each gap and an additional 0.10 penalty for each symbol in each gap; and (3) no penalty for end gaps. Other programs used by those skilled in the art of sequence comparison may also be used, such as, for example, the BLASTN program version 2.0.9, available for use via the National Library of Medicine website ncbi.nlm.nih.gov/gorf/wblast2.cgi, or the UW-BLAST 2.0 algorithm. Standard default parameter settings for UW-BLAST 2.0 are described at the following Internet webpage: blast.wustl.edu/blast/README.html#References. In addition, the BLAST algorithm uses the BLOSUM64 amino acid scoring matix, and optional parameters that may be used are as follows: (A) inclusion of a filter to mask segments of the query sequence that have low compositional complexity (as determined by the SEG program of Wootton & Federhen (Computers and Chemistry, 1993); also see Wootton J C and Federhen S, 1996, Analysis of compositionally biased regions in sequence databases, *Methods Enzymol.* 266: 554–71) or segments consisting of short-periodicity internal repeats (as determined by the XNU program of Claverie & States (Computers and Chemistry, 1993)), and (B) a statistical significance threshold for reporting matches against database sequences, or E-score (the expected probability of matches being found merely by chance, according to the stochastic model of Karlin and Altschul (1990); if the statistical significance ascribed to a match is greater than this E-score threshold, the match will not be reported.); preferred E-score threshold values are 0.5, or in order of increasing preference, 0.25, 0.1, 0.05, 0.01, 0.001, 0.0001, 1e-5, 1e-10, 1e-15, 1e-20, 1e-25, 1e-30, 1e-40, 1e-50, 1e-75, or 1e-100.

The present invention also provides for soluble forms of Claudin polypeptides of the invention comprising certain fragments or domains of these polypeptides, and particularly those comprising the extracellular domain or one or more fragments of the extracellular domain. Soluble polypeptides are polypeptides that are capable of being secreted from the cells in which they are expressed. In such forms part or all of the intracellular and transmembrane domains of the polypeptide are deleted such that the polypeptide is fully secreted from the cell in which it is expressed. The intracellular and transmembrane domains of polypeptides of the invention can be identified in accordance with known techniques for determination of such domains from sequence information. Soluble Claudin polypeptides of the invention also include those polypeptides which include part of the transmembrane region, provided that the soluble human Claudin-19, -21, and -22 polypeptide is capable of being secreted from a cell, and preferably retains human Claudin-19, -21, and -22 activity. Soluble Claudin polypeptides of the invention further include oligomers or fusion polypeptides comprising the extracellular portion of at least one human Claudin-19, -21, and -22 polypeptide, and fragments of any of these polypeptides that have human Claudin-19, -21, and -22 activity. A secreted soluble polypeptide may be identified (and distinguished from its non-soluble membrane-bound counterparts) by separating intact cells which express the desired polypeptide from the culture medium, e.g., by centrifugation, and assaying the medium (supernatant) for the presence of the desired polypeptide. The presence of the desired polypeptide in the medium indicates that the polypeptide was secreted from the cells and thus is a soluble form of the polypeptide. The use of soluble forms of Claudin polypeptides of the invention is advantageous for many applications. Purification of the polypeptides from recombinant host cells is facilitated, since the soluble polypeptides are secreted from the cells. Moreover, soluble polypeptides are generally more suitable than membrane-bound forms for parenteral administration and for many enzymatic procedures.

In another aspect of the invention, preferred polypeptides comprise various combinations of human Claudin-19, -21, and -22 polypeptide domains, such as the cytoplasmic tail domain and the extracellular loop domain. Accordingly, polypeptides of the present invention and nucleic acids encoding them include those comprising or encoding two or more copies of a domain such as the cytoplasmic tail domain, two or more copies of a domain such as the extracellular loop domain, or at least one copy of each domain, and these domains may be presented in any order within such polypeptides.

Further modifications in the peptide or DNA sequences can be made by those skilled in the art using known techniques. Modifications of interest in the polypeptide sequences may include the alteration, substitution, replacement, insertion or deletion of a selected amino acid. For example, one or more of the cysteine residues may be deleted or replaced with another amino acid to alter the conformation of the molecule, an alteration which may involve preventing formation of incorrect intramolecular disulfide bridges upon folding or renaturation. Techniques for such alteration, substitution, replacement, insertion or deletion are well known to those skilled in the art (see, e.g., U.S. Pat No. 4,518,584). As another example, N-glycosylation sites in the polypeptide extracellular domain can be modified to preclude glycosylation, allowing expression of a reduced carbohydrate analog in mammalian and yeast expression systems. N-glycosylation sites in eukaryotic polypeptides are characterized by an amino acid triplet Asn-X—Y, wherein X is any amino acid except Pro and Y is Ser or Thr. Appropriate substitutions, additions, or deletions to the nucleotide sequence encoding these triplets will result in prevention of attachment of carbohydrate residues at the Asn side chain. Alteration of a single nucleotide, chosen so that Asn is replaced by a different amino acid, for example, is sufficient to inactivate an N-glycosylation site. Alternatively, the Ser or Thr can by replaced with another amino acid, such as Ala. Known procedures for inactivating N-glycosylation sites in polypeptides include those described in U.S. Pat. No. 5,071,972 and EP 276,846, hereby incorporated by reference. Additional variants within the scope of the invention include polypeptides that can be modified to create derivatives thereof by forming covalent or aggregative conjugates with other chemical moieties, such as glycosyl groups, lipids, phosphate, acetyl groups and the like. Covalent derivatives can be prepared by lining the chemical moieties to functional groups on amino acid side chains or at the N-terminus or C-terminus of a polypeptide. Conjugates comprising diagnostic (detectable) or therapeutic agents attached thereto are contemplated herein. Preferably, such alteration, substitution, replacement, insertion or deletion retains the desired activity of the polypeptide or a substantial equivalent thereof. One example is a variant that binds with essentially the same binding affinity as does the native form. Binding affinity can be measured by conventional procedures, e.g., as described in U.S. Pat. No. 5,512,457 and as set forth herein.

Other derivatives include covalent or aggregative conjugates of the polypeptides with other polypeptides or polypeptides, such as by synthesis in recombinant culture as N-terminal or C-terminal fusions. Examples of fusion polypeptides are discussed below in connection with oligomers. Further, fusion polypeptides can comprise peptides added to facilitate purification and identification. Such peptides include, for example, poly-His or the antigenic identification peptides described in U.S. Pat. No. 5,011,912 and in Hopp et al., *Bio/Technology* 6:1204, 1988. One such peptide is the FLAG® peptide, which is highly antigenic and provides an epitope reversibly bound by a specific monoclonal antibody, enabling rapid assay and facile purification of expressed recombinant polypeptide. A murine hybridoma designated. 4E11 produces a monoclonal antibody that binds the FLAG® peptide in the presence of certain divalent metal cations, as described in U.S. Pat. No. 5,011,912, hereby incorporated by reference. The 4E11 hybridoma cell line has been deposited with the American Type Culture Collection under accession no. HB 9259. Monoclonal antibodies that bind the FLAG® peptide are available from Eastman Kodak Co., Scientific Imaging Systems Division, New Haven, Conn.

Encompassed by the invention are oligomers or fusion polypeptides that contain a human Claudin-19, -21, and -22 polypeptide, one or more fragments of Claudin polypeptides of the invention, or any of the derivative or variant forms of Claudin polypeptides of the invention as disclosed herein. In particular embodiments, the oligomers comprise soluble Claudin polypeptides of the invention. Oligomers can be in the form of covalently linked or non-covalently-linked multimers, including dimers, trimers, or higher oligomers. In one aspect of the invention, the oligomers maintain the binding ability of the polypeptide components and provide therefor, bivalent, trivalent, etc., binding sites. In an alternative embodiment the invention is directed to oligomers comprising multiple Claudin polypeptides of the invention joined via covalent or non-covalent interactions between peptide moieties fused to the polypeptides, such peptides having the property of promoting oligomerization. Leucine zippers and certain polypeptides derived from antibodies are among the peptides that can promote oligomerization of the polypeptides attached thereto, as described in more detail below.

In embodiments where variants of the Claudin polypeptides of the invention are constructed to include a membrane-spanning domain, they will form a Type I membrane polypeptide. Membrane-spanning Claudin polypeptides of the invention can be fused with extracellular domains of receptor polypeptides for which the ligand is known. Such fusion polypeptides can then be manipulated to control the intracellular signaling pathways triggered by the membrane-spanning human Claudin-19, -21, and -22 polypeptide. Claudin polypeptides of the invention that span the cell membrane can also be fused with agonists or antagonists of cell-surface receptors, or cellular adhesion molecules to further modulate human Claudin-19, -21, and -22 intracellular effects. In another aspect of the present invention, interleukins can be situated between the preferred human Claudin-19, -21, and -22 polypeptide fragment and other fusion polypeptide domains.

Immunoglobulin-based Oligomers. The polypeptides of the invention or fragments thereof may be fused to molecules such as immunoglobulins for many purposes, including increasing the valency of polypeptide binding sites. For example, fragments of a human Claudin-19, -21, and -22 polypeptide may be fused directly or through linker sequences to the Fc portion of an immunoglobulin. For a bivalent form of the polypeptide, such a fusion could be to the Fc portion of an IgG molecule. Other immunoglobulin isotypes may also be used to generate such fusions. For example, a polypeptide-IgM fusion would generate a decavalent form of the polypeptide of the invention. The term "Fc polypeptide" as used herein includes native and mutein forms of polypeptides made up of the Fc region of an antibody comprising any or all of the CH domains of the Fc region. Truncated forms of such polypeptides containing the hinge region that promotes dimerization are also included. Preferred Fc polypeptides comprise an Fc polypeptide derived from a human IgG1 antibody. As one alternative, an oligomer is prepared using polypeptides derived from immunoglobulins. Preparation of fusion polypeptides comprising certain heterologous polypeptides fused to various portions of antibody-derived polypeptides (including the Fc domain) has been described, e.g., by Ashkenazi et al. (*PNAS USA* 88:10535, 1991); Byrn et al. (*Nature* 344:677, 1990); and Hollenbaugh and Aruffo ("Construction of Immunoglobulin Fusion Polypeptides", in *Current Protocols in Immunology*, Suppl. 4, pages 10.19.1–10.19.11, 1992). Methods for preparation and use of immunoglobulin-based oligomers are well known in the art. One embodiment of the present invention is directed to a dimer comprising two fusion polypeptides created by fusing a polypeptide of the invention to an Fc polypeptide derived from an antibody. A gene fusion encoding the polypeptide/Fc fusion polypeptide is inserted into an appropriate expression vector. Polypeptide/Fc fusion polypeptides are expressed in host cells transformed with the recombinant expression vector, and allowed to assemble much like antibody molecules, whereupon interchain disulfide bonds form between the Fc moieties to yield divalent molecules. One suitable Fc polypeptide, described in PCT application WO 93/10151 (hereby incorporated by reference), is a single chain polypeptide extending from the N-terminal hinge region to the native C-terminus of the Fc region of a human IgG1 antibody. Another useful Fc polypeptide is the Fc mutein described in U.S. Pat. No. 5,457,035 and in Baum et al., (*EMBO J.* 13:3992–4001, 1994) incorporated herein by reference. The amino acid sequence of this mutein is identical to that of the native Fc sequence presented in WO 93/10151, except that amino acid 19 has been changed from Leu to Ala, amino acid 20 has been changed from Leu to Glu, and amino acid 22 has been changed from Gly to Ala. The mutein exhibits reduced affinity for Fc receptors. The above-described fusion polypeptides comprising Fc moieties (and oligomers formed therefrom) offer the advantage of facile purification by affinity chromatography over Polypeptide A or Polypeptide G columns. In other embodiments, the polypeptides of the invention can be substituted for the variable portion of an antibody heavy or light chain. If fusion polypeptides are made with both heavy and light chains of an antibody, it is possible to form an oligomer with as many as four human Claudin-19, -21, and -22 extracellular regions.

Peptide-linker Based Oligomers. Alternatively, the oligomer is a fusion polypeptide comprising multiple Claudin polypeptides of the invention, with or without peptide linkers (spacer peptides). Among the suitable peptide linkers are those described in U.S. Pat. Nos. 4,751,180 and 4,935,233, which are hereby incorporated by reference. A DNA sequence encoding a desired peptide linker can be inserted between, and in the same reading frame as, the DNA sequences of the invention, using any suitable conventional technique. For example, a chemically synthesized oligonucleotide encoding the linker can be ligated between the sequences. In particular embodiments, a fusion polypeptide comprises from two to four soluble Claudin polypeptides of the invention, separated by peptide linkers. Suitable peptide linkers, their combination with other polypeptides, and their use are well known by those skilled in the art Leucine-Zippers. Another method for preparing the oligomers of the invention involves use of a leucine zipper. Leucine zipper domains are peptides that promote oligomerization of the polypeptides in which they are found. Leucine zippers were originally identified in several DNA-binding polypeptides (Landschulz et al., *Science* 240:1759, 1988), and have since been found in a variety of different polypeptides. Among the known leucine zippers are naturally occurring peptides and derivatives thereof that dimerize or trimerize. The zipper domain (also referred to herein as an oligomerizing, or oligomer-forming, domain) comprises a repetitive heptad repeat, often with four or five leucine residues interspersed with other amino acids. Use of leucine zippers and preparation of oligomers using leucine zippers are well known in the art.

Other fragments and derivatives of the sequences of polypeptides which would be expected to retain polypeptide activity in whole or in part and may thus be useful for screening or other immunological methodologies may also be made by those skilled in the art given the disclosures herein. Such modifications are believed to be encompassed by the present invention.

Nucleic Acids Encoding Claudin Polypeptides of the Invention

Encompassed within the invention are nucleic acids encoding Claudin polypeptides of the invention. These nucleic acids can be identified in several ways, including isolation of genomic or cDNA molecules from a suitable source. Nucleotide sequences corresponding to the amino acid sequences described herein, to be used as probes or primers for the isolation of nucleic acids or as query sequences for database searches, can be obtained by "back-translation" from the amino acid sequences, or by identification of regions of amino acid identity with polypeptides for which the coding DNA sequence has been identified. The well-known polymerase chain reaction (PCR) procedure can be employed to isolate and amplify a DNA sequence encoding a human Claudin-19, -21, and -22 polypeptide or a desired combination of human Claudin-19, -21, and -22 polypeptide fragments. Oligonucleotides that define the desired termini of the combination of DNA fragments are employed as 5' and 3' primers. The oligonucleotides can additionally contain recognition sites for restriction endonucleases, to facilitate insertion of the amplified combination of DNA fragments into an expression vector. PCR techniques are described in Saiki et al., *Science* 239:487 (1988); *Recombinant DNA Methodology*, Wu et al., eds., Academic Press, Inc., San Diego (1989), pp. 189–196; and *PCR Protocols: A Guide to Methods and Applications*, Innis et. al, eds., Academic Press, Inc. (1990).

Nucleic acid molecules of the invention include DNA and RNA in both single-stranded and double-stranded form, as well as the corresponding complementary sequences. DNA includes, for example, cDNA, genomic DNA, chemically synthesized DNA, DNA amplified by PCR, and combinations thereof. The nucleic acid molecules of the invention include full-length genes or cDNA molecules as well as a combination of fragments thereof. The nucleic acids of the invention are preferentially derived from human sources, but the invention includes those derived from non-human species, as well.

"An isolated nucleic acid consisting essentially of a nucleotide sequence" means that the nucleic acid may have, in addition to said nucleotide sequence, additional material covalently linked to either or both ends of the nucleic acid molecule, said additional material preferably between 1 and 100,000 additional nucleotides covalently linked to either end, each end, or both ends of the nucleic acid molecule, and more preferably between 1 and 10,000 additional nucleotides covalently linked to either end, each end, or both ends of the nucleic acid molecule, and most preferably between 10 and 1,000 additional nucleotides covalently linked to either end, each end, or both ends of the nucleic acid molecule. An isolated nucleic acid consisting essentially of a nucleotide sequence may be an expression vector or other construct comprising said nucleotide sequence.

An "isolated nucleic acid" is a nucleic acid that has been separated from adjacent genetic sequences present in the genome of the organism from which the nucleic acid was isolated, in the case of nucleic acids isolated from naturally-occurring sources. In the case of nucleic acids synthesized enzymatically from a template or chemically, such as PCR products, cDNA molecules, or oligonucleotides for example, it is understood that the nucleic acids resulting from such processes are isolated nucleic acids. An isolated nucleic acid molecule refers to a nucleic acid molecule in the form of a separate fragment or as a component of a larger nucleic acid construct. In one preferred embodiment, the invention relates to certain isolated nucleic acids that are substantially free from contaminating endogenous material. The nucleic acid molecule has preferably been derived from DNA or RNA isolated at least once in substantially pure form and in a quantity or concentration enabling identification, manipulation, and recovery of its component nucleotide sequences by standard biochemical methods (such as those outlined in Sambrook et al., *Molecular Cloning: A Laboratory Manual*, 2nd sed., Cold Spring Harbor Laboratory, Cold Spring Harbor, N.Y. (1989)). Such sequences are preferably provided and/or constructed in the form of an open reading frame uninterrupted by internal non-translated sequences, or introns, that are typically present in eukaryotic genes. Sequences of non-translated DNA can be present 5' or 3' from an open reading frame, where the same do not interfere with manipulation or expression of the coding region.

The present invention also includes nucleic acids that hybridize under moderately stringent conditions, and more preferably highly stringent conditions, to nucleic acids encoding Claudin polypeptides of the invention described herein. The basic parameters affecting the choice of hybridization conditions and guidance for devising suitable conditions are set forth by Sambrook, J., E. F. Fritsch, and T. Maniatis (1989, Molecular Cloning: A Laboratory Manual, Cold Spring Harbor Laboratory Press, Cold Spring Harbor, N.Y., chapters 9 and 11; and Current Protocols in Molecular Biology, 1995, F. M. Ausubel et al., eds., John Wiley & Sons, Inc., sections 2.10 and 6.3–6.4, incorporated herein by reference), and can be readily determined by those having ordinary skill in the art based on, for example, the length and/or base composition of the DNA. One way of achieving moderately stringent conditions involves the use of a prewashing solution containing 5×SSC, 0.5% SDS, 1.0 mM EDTA (pH 8.0), hybridization buffer of about 50% formamide, 6×SSC, and a hybridization temperature of about 55 degrees C. (or other similar hybridization solutions, such as one containing about 50% formamide, with a hybridization temperature of about 42 degrees C.), and washing conditions of about 60 degrees C., in 0.5×SSC, 0.1% SDS. Generally, highly stringent conditions are defined as hybridization conditions as above, but with washing at approximately 68 degrees C., 0.2×SSC, 0.1% SDS. SSPE (1×SSPE is 0.15M NaCl, 10 mM NaH$_2$PO$_4$, and 125 mM EDTA, pH 7.4) can be substituted for SSC (1×SSC is 0.15M NaCl and 15 mM sodium citrate) in the hybridization and wash buffers; washes are performed for 15 minutes after hybridization is complete. It should be understood that the wash temperature and wash salt concentration can be adjusted as necessary to achieve a desired degree of stringency by applying the basic principles that govern hybridization reactions and duplex stability, as known to those skilled in the art and described further below (see, e.g., Sambrook et al., 1989). When hybridizing a nucleic acid to a target nucleic acid of unknown sequence, the hybrid length is assumed to be that of the hybridizing nucleic acid. When nucleic acids of known sequence are hybridized, the hybrid length can be determined by aligning the sequences of the nucleic acids and identifying the region or regions of optimal sequence complementarity. The hybridization temperature for hybrids anticipated to be less than 50 base pairs in length should be 5 to 10.degrees C. less than the melting temperature (Tm) of the hybrid, where Tm is determined according to the following equations. For hybrids less than 18 base pairs in length, Tm (degrees C.)=2(# of A+T bases)+4(# of #G+C bases). For hybrids above 18 base pairs in length, Tm (degrees C.)=81.5+16.6($\log_{10}$ [Na$^+$])+0.41(% G+C)−(600/N), where N is the number of bases in the hybrid, and [Na$^+$] is the concentration of sodium ions in the hybridization buffer ([Na$^+$] for 1×SSC=0.165M). Preferably, each such hybridizing nucleic acid has a length that is at least 15, 18, 20, 25, 30, 40, or more preferably 50 nucleotides, or at least 25% (more preferably at least 50%, or at least 60%, or at least 70%, and most preferably at least 80%) of the length of the nucleic acid of the present invention to which it hybridizes, and has at least 60% sequence identity (more preferably at least 70%, at least 75%, at least 80%, at least 85%, at least 90%, at least 95%, at least 97.5%, or a 99%, and most preferably at least 99.5%) with the nucleic acid of the present invention to which it hybridizes, where sequence identity is determined by comparing the sequences of the hybridizing nucleic acids when aligned so as to maximize overlap and identity while minimizing sequence gaps as described in more detail above.

The present invention also provides genes corresponding to the nucleic acid sequences disclosed herein. "Corresponding genes" are the regions of the genome that are transcribed to produce the mRNAs from which cDNA nucleic acid sequences are derived and may include contiguous regions of the genome necessary for the regulated expression of such genes. Corresponding genes may therefore include but are not limited to coding sequences, 5' and 3' untranslated regions, alternatively spliced exons, introns, promoters, enhancers, and silencer or suppressor elements. The corresponding genes can be isolated in accordance with known methods using the sequence information disclosed herein. Such methods include the preparation of probes or primers from the disclosed sequence information for identification and/or amplification of genes in appropriate genomic libraries or other sources of genomic materials. An "isolated gene" is a gene that has been separated from the adjacent coding sequences, if any, present in the genome of the organism from which the gene was isolated.

Methods for Making and Purifying Claudin Polypeptides of the Invention

Methods for making Claudin polypeptides of the invention are described below. Expression, isolation, and purification of the polypeptides and fragments of the invention can be accomplished by any suitable technique, including but not limited to the following methods.

The isolated nucleic acid of the invention may be operably linked to an expression control sequence such as the pMT2 or pED expression vectors disclosed in Kaufman et al., Nucleic Acids Res. 19, 4485–4490 (1991); and Pouwels et al. *Cloning Vectors: A Laboratory Manual*, Elsevier, N.Y., (1985), in order to produce the polypeptide recombinantly. Many suitable expression control sequences are known in the art. General methods of expressing recombinant polypeptides are also known and are exemplified in R. Kaufman, Methods in Enzymology 185, 537–566 (1990). As used herein "operably linked" means that the nucleic acid of the invention and an expression control sequence are situated within a construct, vector, or cell in such a way that the polypeptide encoded by the nucleic acid is expressed when appropriate molecules (such as polymerases) are present. As one embodiment of the invention, at least one expression control sequence is operably linked to the nucleic acid of the invention in a recombinant host cell or progeny thereof, the nucleic acid and/or expression control sequence having been introduced into the host cell by transformation or transfection, for example, or by any other suitable method. As another embodiment of the invention, at least one expression control sequence is integrated into the genome of a recombinant host cell such that it is operably linked to a nucleic acid sequence encoding a polypeptide of the invention. In a further embodiment of the invention, at least one expression control sequence is operably linked to a nucleic acid of the invention through the action of a trans-acting factor such as a transcription factor, either in vitro or in a recombinant host cell.

In addition, a sequence encoding an appropriate signal peptide (native or heterologous) can be incorporated into expression vectors. The choice of signal peptide or leader can depend on factors such as the type of host cells in which the recombinant polypeptide is to be produced. To illustrate, examples of heterologous signal peptides that are functional in mammalian host cells include the signal sequence for interleukin-7 (IL-7) described in U.S. Pat. No. 4,965,195; the signal sequence for interleukin-2 receptor described in Cosman et al., *Nature* 312:768 (1984); the interleukin-4 receptor signal peptide described in EP 367,566; the type I interleukin-1 receptor signal peptide described in U.S. Pat. No. 4,968,607; and the type II interleukin-1 receptor signal peptide described in EP 460,846. A DNA sequence for a signal peptide (secretory leader) can be fused in frame to the nucleic acid sequence of the invention so that the DNA is initially transcribed, and the mRNA translated, into a fusion polypeptide comprising the signal peptide. A signal peptide that is functional in the intended host cells promotes extracellular secretion of the polypeptide. The signal peptide is cleaved from the polypeptide upon secretion of polypeptide from the cell. The skilled artisan will also recognize that the position(s) at which the signal peptide is cleaved can differ from that predicted by computer program, and can vary according to such factors as the type of host cells employed in expressing a recombinant polypeptide. A polypeptide preparation can include a mixture of polypeptide molecules having different N-terminal amino acids, resulting from cleavage of the signal peptide at more than one site.

Established methods for introducing DNA into mammalian cells have been described (Kaufman, R J., *Large Scale Mammalian Cell Culture*, 1990, pp. 15–69). Additional protocols using commercially available reagents, such as Lipofectamine lipid reagent (Gibco/BRL) or Lipofectamine-Plus lipid reagent, can be used to transfect cells (Felgner et al., *Proc. Natl. Acad. Sci. USA* 84:7413–7417, 1987). In addition, electroporation can be used to transfect mammalian cells using conventional procedures, such as those in Sambrook et al. (*Molecular Cloning: A Laboratory Manual*, 2 ed. Vol. 1-3, Cold Spring Harbor Laboratory Press, 1989). Selection of stable transformants can be performed using methods known in the art, such as, for example, resistance to cytotoxic drugs. Kaufman et al., *Meth. in Enzymology* 185:487–511, 1990, describes several selection schemes, such as dihydrofolate reductase (DHFR) resistance. A suitable strain for DHFR selection can be CHO strain DX-B11, which is deficient in DHFR (Urlaub and Chasin, *Proc. Natl. Acad. Sci. USA* 77:4216–4220, 1980). A plasmid expressing the DHFR cDNA can be introduced into strain DX-B11, and only cells that contain the plasmid can grow in the appropriate selective media. Other examples of selectable markers that can be incorporated into an expression vector include cDNAs conferring resistance to antibiotics, such as G418 and hygromycin B. Cells harboring the vector can be selected on the basis of resistance to these compounds.

Alternatively, gene products can be obtained via homologous recombination, or "gene targeting," techniques. Such techniques employ the introduction of exogenous transcription control elements (such as the CMV promoter or the like) in a particular predetermined site on the genome, to induce expression of the endogenous nucleic acid sequence of interest The location of integration into a host chromosome or genome can be easily determined by one of skill in the art, given the known location and sequence of the gene. In a preferred embodiment, the present invention also contemplates the introduction of exogenous transcriptional control elements in conjunction with an amplifiable gene, to produce increased amounts of the gene product, again, without the need for isolation of the gene sequence itself from the host cell. The practice of homologous recombination or gene targeting is explained by Schimke, et al." *Amplification of Genes in Somatic Mammalian cells*," Methods in Enzymology 151:85–104 (1987), as well as by Capecchi, et al., "*The New Mouse Genetics: Altering the Genome by Gene Targeting*," TIG 5:70–76 (1989).

A number of types of cells may act as suitable host cells for expression of the polypeptide. Mammalian host cells include, for example, the COS-7 line of monkey kidney cells (ATCC CRL 1651) (Gluzman et al., *Cell* 23:175, 1981), L cells, C127 cells, 3T3 cells (ATCC CCL 163), Chinese hamster ovary (CHO) cells, HeLa cells, BHK (ATCC CRL 10) cell lines, the CV1/EBNA cell line derived from the African green monkey kidney cell line CV1 (ATCC CCL 70) as described by McMahan et al. (*EMBO J*. 10: 2821, 1991), human kidney 293 cells, human epidermal A431 cells, human Colo205 cells, other transformed primate cell lines, normal diploid cells, cell strains derived from in vitro culture of primary tissue, primary explants, HL60, U937, HaK or Jurkat cells. Alternatively, it may be possible to produce the polypeptide in lower eukaryotes such as yeast or in prokaryotes such as bacteria. Potentially suitable yeast strains include *Saccharomyces cerevisiae, Schizosaccharomyces pombe,* Kluyveromyces strains, Candida, or any yeast strain capable of expressing heterologous polypeptides. Potentially suitable bacterial strains include *Escherichia coli, Bacillus subtilis, Salmonella typhimurium*, or any bacterial strain capable of expressing heterologous polypeptides. If the polypeptide is made in yeast or bacteria, it may be necessary to modify the polypeptide produced therein, for example by phosphorylation or glycosylation of the appropriate sites, in order to obtain the functional polypeptide. Such covalent attachments may be accomplished using known chemical or enzymatic methods. The polypeptide may also be produced by operably linking the isolated nucleic acid of the invention to suitable control sequences in one or more insect expression vectors, and employing an insect expression system. Materials and methods for baculovirus/insect cell expression systems are commercially available in kit form from, e.g., Invitrogen, San Diego, Calif., U.S.A (the MaxBac® kit), and such methods are well known in the art, as described in Summers and Smith, Texas Agricultural Experiment Station Bulletin No. 1555 (1987), and Luckow and Summers, *Bio/Technology* 6:47 (1988), incorporated herein by reference. As used herein, an insect cell capable of expressing a nucleic acid of the present invention is "transformed." Cell-free translation systems could also be employed to produce polypeptides using RNAs derived from nucleic acid constructs disclosed herein. A host cell that comprises an isolated nucleic acid of the invention, preferably operably linked to at least one expression control sequence, is a "recombinant host cell".

The polypeptide of the invention may be prepared by culturing transformed host cells under culture conditions suitable to express the recombinant polypeptide. The resulting expressed polypeptide may then be purified from such culture (i.e., from culture medium or cell extracts) using known purification processes, such as gel filtration and ion exchange chromatography. The purification of the polypeptide may also include an affinity column containing agents which will bind to the polypeptide; one or more column steps over such affinity resins as concanavalin A-agarose, heparin-toyopearl® or Cibacrom blue 3GA Sepharose®; one or more steps involving hydrophobic interaction chromatography using such resins as phenyl ether, butyl ether, or propyl ether; or immunoaffinity chromatography. Alternatively, the polypeptide of the invention may also be expressed in a form which will facilitate purification. For example, it may be expressed as a fusion polypeptide, such as those of maltose binding polypeptide (MBP), glutathione-S-transferase (GST) or thioredoxin (TRX). Kits for expression and purification of such fusion polypeptides are commercially available from New England BioLab (Beverly, Mass.), Pharmacia (Piscataway, N.J.) and InVitrogen, respectively. The polypeptide can also be tagged with an epitope and subsequently purified by using a specific antibody directed to such epitope. One such epitope ("Flag") is commercially available from Kodak (New Haven, Conn.). Finally, one or more reverse-phase high performance liquid chromatography (RP-HPLC) steps employing hydrophobic RP-HPLC media, e.g., silica gel having pendant methyl or other aliphatic groups, can be employed to further purify the polypeptide. Some or all of the foregoing purification steps, in various combinations, can also be employed to provide a substantially homogeneous isolated recombinant polypeptide. The polypeptide thus purified is substantially free of other mammalian polypeptides and is defined in accordance with the present invention as an "isolated polypeptide"; such isolated polypeptides of the invention include isolated antibodies that bind to Claudin polypeptides of the invention, fragments, variants, binding partners etc. The polypeptide of the invention may also be expressed as a product of transgenic animals, e.g., as a component of the milk of transgenic cows, goats, pigs, or sheep which are characterized by somatic or germ cells containing a nucleotide sequence encoding the polypeptide.

It is also possible to utilize an affinity column comprising a polypeptide-binding polypeptide of the invention, such as a monoclonal antibody generated against polypeptides of the invention, to affinity-purify expressed polypeptides. These polypeptides can be removed from an affinity column using conventional techniques, e.g., in a high salt elution buffer and then dialyzed into a lower salt buffer for use or by changing pH or other components depending on the affinity matrix utilized, or be competitively removed using the naturally occurring substrate of the affinity moiety, such as a polypeptide derived from the invention. In this aspect of the invention, polypeptide-binding polypeptides, such as the anti-polypeptide antibodies of the invention or other polypeptides that can interact with the polypeptide of the invention, can be bound to a solid phase support such as a column chromatography matrix or a similar substrate suitable for identifying, separating, or purifying cells that express polypeptides of the invention on their surface. Adherence of polypeptide-binding polypeptides of the invention to a solid phase contacting surface can be accomplished by any means, for example, magnetic microspheres can be coated with these polypeptide-binding polypeptides and held in the incubation vessel through a magnetic field. Suspensions of cell mixtures are contacted with the solid phase that has such polypeptide-binding polypeptides thereon. Cells having polypeptides of the invention on their surface bind to the fixed polypeptide-binding polypeptide and unbound cells then are washed away. This affinity-binding method is useful for purifying, screening, or separating such polypeptide-expressing cells from solution. Methods of releasing positively selected cells from the solid phase are known in the art and encompass, for example, the use of enzymes. Such enzymes are preferably non-toxic and non-injurious to the cells and are preferably directed to cleaving the cell-surface binding partner. Alternatively, mixtures of cells suspected of containing polypeptide-expressing cells of the invention first can be incubated with a biotinylated polypeptide-binding polypeptide of the invention. Incubation periods are typically at least one hour in duration to ensure sufficient binding to polypeptides of the invention. The resulting mixture then is passed through a column packed with avidin-coated beads, whereby the high affinity of biotin for avidin provides the binding of the polypeptide-binding cells to the beads. Use of avidin-coated beads is known in the art. See Berenson, et al. *J. Cell. Biochem.*, 10D:239 (1986). Wash of unbound material and the release of the bound cells is performed using conventional methods The polypeptide may also be produced by known conventional chemical synthesis. Methods for constructing the polypeptides of the present invention by synthetic means are known to those skilled in the art. The synthetically-constructed polypeptide sequences, by virtue of sharing primary, secondary or tertiary structural and/or conformational characteristics with polypeptides may possess biological properties in common therewith, including polypeptide activity. Thus, they may be employed as biologically active or immunological substitutes for natural, purified polypeptides in screening of therapeutic compounds and in immunological processes for the development of antibodies.

The desired degree of purity depends on the intended use of the polypeptide. A relatively high degree of purity is desired when the polypeptide is to be administered in vivo, for example. In such a case, the polypeptides are purified such that no polypeptide bands corresponding to other polypeptides are detectable upon analysis by SDS-polyacrylamide gel electrophoresis (SDS-PAGE). It will be recognized by one skilled in the pertinent field that multiple bands corresponding to the polypeptide can be visualized by SDS-PAGE, due to differential glycosylation, differential post-translational processing, and the like. Most preferably, the polypeptide of the invention is purified to substantial homogeneity, as indicated by a single polypeptide band upon analysis by SDS-PAGE. The polypeptide band can be visualized by silver staining, Coomassie blue staining, or (if the polypeptide is radiolabeled) by autoradiography.

Antagonists and Agonists of Claudin Polypeptides of the Invention

Any method which neutralizes Claudin polypeptides of the invention or inhibits expression of the human Claudin-19, -21, and -22 genes (either transcription or translation) can be used to reduce the biological activities of Claudin polypeptides of the invention. In particular embodiments, antagonists inhibit the binding of at least one human Claudin-19, -21, and -22 polypeptide to binding partners expressed on cells, thereby inhibiting biological activities induced by the binding of those Claudin polypeptides of the invention to the cells. In certain other embodiments of the invention, antagonists can be designed to reduce the level of endogenous human Claudin-19, -21, and -22 gene expression, e.g., using well-known antisense or ribozyme approaches to inhibit or prevent translation of human Claudin-19, -21, and -22 mRNA transcripts; triple helix approaches to inhibit transcription of human Claudin-19, -21, and -22 genes; or targeted homologous recombination to inactivate or "knock out" the human Claudin-19, -21, and -22 genes or their endogenous promoters or enhancer elements. Such antisense, ribozyme, and triple helix antagonists may be designed to reduce or inhibit either unimpaired, or if appropriate, mutant human Claudin-19, -21, and -22 gene activity. Techniques for the production and use of such molecules are well known to those of skill in the art.

Antisense RNA and DNA molecules act to directly block the translation of mRNA by hybridizing to targeted mRNA and preventing polypeptide translation. Antisense approaches involve the design of oligonucleotides (either DNA or RNA) that are complementary to a human Claudin-19, -21, and -22 mRNA. The antisense oligonucleotides will bind to the complementary target gene mRNA transcripts and prevent translation. Absolute complementarity, although preferred, is not required. A sequence "complementary" to a portion of a nucleic acid, as referred to herein, means a sequence having sufficient complementarity to be able to hybridize with the nucleic acid, forming a stable duplex (or triplex, as appropriate). In the case of double-stranded antisense nucleic acids, a single strand of the duplex DNA may thus be tested, or triplex formation may be assayed. The ability to hybridize will depend on both the degree of complementarity and the length of the antisense nucleic acid. Oligonucleotides that are complementary to the 5' end of the message, e.g., the 5' untranslated sequence up to and including the AUG initiation codon, should work most efficiently at inhibiting translation. However, oligonucleotides complementary to either the 5'- or 3'-non-translated, non-coding regions of the human Claudin-19, -21, and -22 gene transcript could be used in an antisense approach to inhibit translation of endogenous human Claudin-19, -21, and -22 mRNA. Oligonucleotides complementary to the 5' untranslated region of the mRNA should include the complement of the AUG start codon. Antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides. The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., 1989, Proc. Natl. Acad. Sci. U.S.A 86:6553–6556; Lemaitre et al., 1987, Proc. Natl. Acad. Sci. 84:648–652; PCT Publication No. WO88/09810, published Dec. 15, 1988), or hybridization-triggered cleavage agents or intercalating agents. (See, e.g., Zon, 1988, Pharm. Res. 5:539–549). The antisense molecules should be delivered to cells which express the human Claudin-19, -21, and -22 transcript in vivo. A number of methods have been developed for delivering antisense DNA or RNA to cells; e.g., antisense molecules can be injected directly into the tissue or cell derivation site, or modified antisense molecules, designed to target the desired cells (e.g., antisense linked to peptides or antibodies that specifically bind receptors or antigens expressed on the target cell surface) can be administered systemically. However, it is often difficult to achieve intracellular concentrations of the antisense sufficient to suppress translation of endogenous mRNAs. Therefore a preferred approach utilizes a recombinant DNA construct in which the antisense oligonucleotide is placed under the control of a strong pol III or pol II promoter. The use of such a construct to transfect target cells in the patient will result in the transcription of sufficient amounts of single stranded RNAs that will form complementary base pairs with the endogenous human Claudin-19, -21, and -22 gene transcripts and thereby prevent translation of the human Claudin-19, -21, and -22 mRNA. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells.

Ribozyme molecules designed to catalytically cleave human Claudin-19, -21, and -22 mRNA transcripts can also be used to prevent translation of human Claudin-19, -21, and -22 nRNA and expression of Claudin polypeptides of the invention. (See, e.g., PCT International Publication WO90/11364, published Oct. 4, 1990; U.S. Pat. No. 5,824,519). The ribozymes that can be used in the present invention include hammerhead ribozymes (Haseloff and Gerlach, 1988, Nature, 334:585–591), RNA endoribonucleases (hereinafter "Cech-type ribozymes") such as the one which occurs naturally in Tetrahymena Thermophila (known as the IVS, or L-19 IVS RNA) and which has been extensively described by Thomas Cech and collaborators (International Patent Application No. WO 88/04300; Been and Cech, 1986, Cell, 47:207–216). As in the antisense approach, the ribozymes can be composed of modified oligonucleotides (e.g. for improved stability, targeting, etc.) and should be delivered to cells which express the human Claudin-19, -21, and -22 polypeptide in vivo. A preferred method of delivery involves using a DNA construct "encoding" the ribozyme under the control of a strong constitutive pol III or pol II promoter, so that transfected cells will produce sufficient quantities of the ribozyme to destroy endogenous human Claudin-19, -21, and -22 messages and inhibit translation. Because ribozymes, unlike antisense molecules, are catalytic, a lower intracellular concentration is required for efficiency.

Alternatively, endogenous human Claudin-19, -21, and -22 gene expression can be reduced by targeting deoxyribonucleotide sequences complementary to the regulatory region of the target gene (i.e., the target gene promoter and/or enhancers) to form triple helical structures that prevent transcription of the target human Claudin-19, -21, and -22 gene. (See generally, Helene, 1991, Anticancer Drug Des., 6(6), 569–584; Helene, et al., 1992, Ann. N.Y. Acad. Sci., 660, 27–36; and Maher, 1992, Bioassays 14(12), 807–815).

Anti-sense RNA and DNA, ribozyme, and triple helix molecules of the invention may be prepared by any method known in the art for the synthesis of DNA and RNA molecules. These include techniques for chemically synthesizing oligodeoxyribonucleotides and oligoribonucleotides well known in the art such as for example solid phase phosphoramidite chemical synthesis. Oligonucleotides can be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al., 1988, Nucl. Acids Res. 16:3209. Methylphosphonate oligonucleotides can be prepared by use of controlled pore glass polymer supports (Sarin et al., 1988, Proc. Natl. Acad. Sci. U.S.A. 85:7448–7451). Alternatively, RNA molecules may be generated by in vitro and in vivo transcription of DNA sequences encoding the antisense RNA molecule. Such DNA sequences may be incorporated into a wide variety of vectors that incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Endogenous target gene expression can also be reduced by inactivating or "knocking out" the target gene or its promoter using targeted homologous recombination (e.g., see Smithies, et al., 1985, Nature 317, 230–234; Thomas and Capecchi, 1987, Cell 51, 503–512; Thompson, et al., 1989, Cell 5, 313–321; each of which is incorporated by reference herein in its entirety). For example, a mutant, non-functional target gene (or a completely unrelated DNA sequence) flanked by DNA homologous to the endogenous target gene (either the coding regions or regulatory regions of the target gene) can be used, with or without a selectable marker and/or a negative selectable marker, to transfect cells that express the target gene in vivo. Insertion of the DNA construct, via targeted homologous recombination, results in inactivation of the target gene. Such approaches are particularly suited in the agricultural field where modifications to ES (embryonic stem) cells can be used to generate animal offspring with an inactive target gene (e.g., see Thomas and Capecchi, 1987 and Thompson, 1989, supra), or in model organisms such as *Caenorhabditis elegans* where the "RNA interference" ("RNAi") technique (Grishok A, Tabara H, and Mello CC, 2000, Genetic requirements for inheritance of RNAi in *C. elegans*, Science 287 (5462): 2494–2497), or the introduction of transgenes (Dernburg A F, Zalevsky J, Colaiacovo M P, and Villeneuve A M, 2000, Transgene-mediated cosuppression in the *C. elegans* germ line, Genes Dev. 14 (13): 1578–1583) are used to inhibit the expression of specific target genes. However this approach can be adapted for use in humans provided the recombinant DNA constructs are directly administered or targeted to the required site in vivo using appropriate viral vectors.

Organisms that have enhanced, reduced, or modified expression of the gene(s) corresponding to the nucleic acid sequences disclosed herein are provided. The desired change in gene expression can be achieved through the use of antisense nucleic acids or ribozymes that bind and/or cleave the mRNA transcribed from the gene (Albert and Morris, 1994, Trends Pharmacol. Sci. 15(7): 250–254; Lavarosky et al., 1997, Biochem. Mol. Med. 62(1): 11–22; and Hampel, 1998, Prog. Nucleic Acid Res. Mol. Biol. 58: 1–39; all of which are incorporated by reference herein). Transgenic animals that have multiple copies of the gene(s) corresponding to the nucleic acid sequences disclosed herein, preferably produced by transformation of cells with genetic constructs that are stably maintained within the transformed cells and their progeny, are provided. Transgenic animals that have modified genetic control regions that increase or reduce gene expression levels, or that change temporal or spatial patterns of gene expression, are also provided (see European Patent No. 0 649 464 B1, incorporated by reference herein). In addition, organisms are provided in which the gene(s) corresponding to the nucleic acid sequences disclosed herein have been partially or completely inactivated, through insertion of extraneous sequences into the corresponding gene(s) or through deletion of all or part of the corresponding gene(s). Partial or complete gene inactivation can be accomplished through insertion, preferably followed by imprecise excision, of transposable elements (Plasterk, 1992, Bioessays 14(9): 629–633; Zwaal et al., 1993, Proc. Natl. Acad. Sci. USA 90(16): 7431–7435; Clark et al., 1994, Natl. Acad. Sci. USA 91(2): 719–722; all of which are incorporated by reference herein), or through homologous recombination, preferably detected by positive/negative genetic selection strategies (Mansour et al., 1988, Nature 336: 348–352; U.S. Pat. Nos. 5,464,764; 5,487,992; 5,627,059; 5,631,153; 5,614,396; 5,616,491; and 5,679,523; all of which are incorporated by reference herein). These organisms with altered gene expression are preferably eukaryotes and more preferably are mammals. Such organisms are useful for the development of non-human models for the study of disorders involving the corresponding gene(s), and for the development of assay systems for the identification of molecules that interact with the polypeptide product(s) of the corresponding gene(s).

The Claudin polypeptides of the invention themselves can also be employed in inhibiting a biological activity of human Claudin-19, -21, and -22 in in vitro or in vivo procedures. Encompassed within the invention are extracellular loop domains of Claudin polypeptides of the invention that act as "dominant negative" inhibitors of native human Claudin-19, -21, and -22 polypeptide function when expressed as fragments or as components of fusion polypeptides. For example, a purified polypeptide domain of the present invention can be used to inhibit binding of Claudin polypeptides of the invention to endogenous binding partners. Such use effectively would block human Claudin-19, -21, and -22 polypeptide interactions and inhibit human Claudin-19, -21, and -22 polypeptide activities. In still another aspect of the invention, a soluble form of the human Claudin-19, -21, and -22 binding partner, which is expressed on epithelial and/or endothelial cells, is used to bind to and competitively inhibit activation of the endogenous human Claudin-19, -21, and -22 polypeptide. Furthermore, antibodies which bind to Claudin polypeptides of the invention often inhibit human Claudin-19, -21, and -22 activity and act as antagonists. For example, antibodies that specifically recognize one or more epitopes of Claudin polypeptides of the invention, or epitopes of conserved variants of Claudin polypeptides of the invention, or peptide fragments of the human Claudin-19, -21, and -22 polypeptide can be used in the invention to inhibit human Claudin-19, -21, and -22 activity. Such antibodies include but are not limited to polyclonal antibodies, monoclonal antibodies (mAbs), humanized or chimeric antibodies, single chain antibodies, Fab fragments, F(ab')2 fragments, fragments produced by a Fab expression library, anti-idiotypic (anti-Id) antibodies, and epitope-binding fragments of any of the above. Alternatively, purified and modified Claudin polypeptides of the invention of the present invention can be administered to modulate interactions between Claudin polypeptides of the invention and human Claudin-19, -21, and -22 binding partners that are not membrane-bound. Such an approach will allow an alternative method for the modification of human Claudin-19, -21, and -22-influenced bioactivity.

In an alternative aspect, the invention further encompasses the use of agonists of human Claudin-19, -21, and -22 activity to treat or ameliorate the symptoms of a disease for which increased human Claudin-19, -21, and -22 activity is beneficial. Such diseases include but are not limited to inflammation, asthma, allergy, metastasis of cancer cells, ion transport disorders such as magnesium transport defects in the kidney, inflammatory bowel disease, exposure to to *Clostridium perfringens* enterotoxin (CPE), sudden infant death syndrome (SIDS), multiple sclerosis (MS), autoimmune encephalomyelitis, optic neuritis, and progressive multifocal leukoencephalopathy (PML). In a preferred aspect, the invention entails administering compositions comprising an human Claudin-19, -21, and -22 nucleic acid or an human Claudin-19, -21, and -22 polypeptide to cells in vitro, to cells ex vivo, to cells in vivo, and/or to a multicellular organism. Preferred therapeutic forms of human Claudin-19, -21, and -22 are soluble forms, as described above. In still another aspect of the invention, the compositions comprise administering a human Claudin-19, -21, and -22-encoding nucleic acid for expression of a human Claudin-19, -21, and -22 polypeptide in a host organism for treatment of disease. Particularly preferred in this regard is expression in a human patient for treatment of a dysfunction associated with aberrant (e.g., decreased) endogenous activity of a human Claudin-19, -21, and -22 polypeptide. Furthermore, the invention encompasses the administration to cells and/or organisms of compounds found to increase the endogenous activity of Claudin polypeptides of the invention. One example of compounds that increase human Claudin-19, -21, and -22 polypeptide activity are agonistic antibodies, preferably monoclonal antibodies, that bind to Claudin polypeptides of the invention or binding partners, which may increase human Claudin-19, -21, and -22 polypeptide activity by causing constitutive intracellular signaling (or "ligand mimicking"), or by preventing the binding of a native inhibitor of human Claudin-19, -21, and -22 polypeptide activity.

Antibodies to Claudin Polypeptides of the Invention

Antibodies that are immunoreactive with the polypeptides of the invention are provided herein. Such antibodies specifically bind to the polypeptides via the antigen-binding sites of the antibody (as opposed to nonspecific binding). In the present invention, specifically binding antibodies are those that will specifically recognize and bind with Claudin polypeptides of the invention, homologues, and variants, but not with other molecules. In one preferred embodiment, the antibodies are specific for the polypeptides of the present invention and do not cross-react with other polypeptides. In this manner, the Claudin polypeptides of the invention, fragments, variants, fusion polypeptides, etc., as set forth above can be employed as "immunogens" in producing antibodies immunoreactive therewith.

More specifically, the polypeptides, fragment, variants, fusion polypeptides, etc. contain antigenic determinants or epitopes that elicit the formation of antibodies. These antigenic determinants or epitopes can be either linear or conformational (discontinuous). Linear epitopes are composed of a single section of amino acids of the polypeptide, while conformational or discontinuous epitopes are composed of amino acids sections from different regions of the polypeptide chain that are brought into close proximity upon polypeptide folding (C. A. Janeway, Jr. and P. Travers, *Immuno Biology* 3:9 (Garland Publishing Inc., 2nd ed. 1996)). Because folded polypeptides have complex surfaces, the number of epitopes available is quite numerous; however, due to the conformation of the polypeptide and steric hinderances, the number of antibodies that actually bind to the epitopes is less than the number of available epitopes (C. A. Janeway, Jr. and P. Travers, *Immuno Biology* 2:14 (Garland Publishing Inc., 2nd ed. 1996)). Epitopes can be identified by any of the methods known in the art. Thus, one aspect of the present invention relates to the antigenic epitopes of the polypeptides of the invention. Such epitopes are useful for raising antibodies, in particular monoclonal antibodies, as described in more detail below. Additionally, epitopes from the polypeptides of the invention can be used as research reagents, in assays, and to purify specific binding antibodies from substances such as polyclonal sera or supernatants from cultured hybridomas. Such epitopes or variants thereof can be produced using techniques well known in the art such as solid-phase synthesis, chemical or enzymatic cleavage of a polypeptide, or using recombinant DNA technology.

As to the antibodies that can be elicited by the epitopes of the polypeptides of the invention, whether the epitopes have been isolated or remain part of the polypeptides, both polyclonal and monoclonal antibodies can be prepared by conventional techniques. See, for example, *Monoclonal Antibodies, Hybridomas: A New Dimension in Biological Analyses*, Kennet et al. (eds.), Plenum Press, New York (1980); and *Antibodies: A Laboratory Manual*, Harlow and Land (eds.), Cold Spring Harbor Laboratory Press, Cold Spring Harbor, N.Y., (1988); Kohler and Milstein, (U.S. Pat. No. 4,376,110); the human B-cell hybridoma technique (Kosbor et al., 1983, Immunology Today 4:72; Cole et al., 1983, Proc. Natl. Acad. Sci. USA 80:2026–2030); and the EBV-hybridoma technique (Cole et al., 1985, Monoclonal Antibodies And Cancer Therapy, Alan R. Liss, Inc., pp. 77–96). Hybridoma cell lines that produce monoclonal antibodies specific for the polypeptides of the invention are also contemplated herein. Such hybridomas can be produced and identified by conventional techniques. The hybridoma producing the mAb of this invention may be cultivated in vitro or in vivo. Production of high titers of mAbs in vivo makes this the presently preferred method of production. One method for producing such a hybridoma cell line comprises immunizing an animal with a polypeptide; harvesting spleen cells from the immunized animal; fusing said spleen cells to a myeloma cell line, thereby generating hybridoma cells; and identifying a hybridoma cell line that produces a monoclonal antibody that binds the polypeptide. For the production of antibodies, various host animals may be immunized by injection with one or more of the following: a human Claudin-19, -21, and -22 polypeptide, a fragment of a human Claudin-19, -21, and -22 polypeptide, a functional equivalent of a human Claudin-19, -21, and -22 polypeptide, or a mutant form of a human Claudin-19, -21, and -22 polypeptide. Such host animals may include but are not limited to rabbits, mice, and rats. Various adjutants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjutants such as BCG (bacille Calmette-Guerin) and *Corynebacterium parvum*. The monoclonal antibodies can be recovered by conventional techniques. Such monoclonal antibodies may be of any immunoglobulin class including IgG, IgM, IgE, IgA, IgD and any subclass thereof.

In addition, techniques developed for the production of "chimeric antibodies" (Takeda et al., 1985, Nature, 314: 452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a porcine mAb and a human immunoglobulin constant region. The monoclonal antibodies of the present invention also include humanized versions of murine monoclonal antibodies. Such humanized antibodies can be prepared by known techniques and offer the advantage of reduced immunogenicity when the antibodies are administered to humans. In one embodiment, a humanized monoclonal antibody comprises the variable region of a murine antibody (or just the antigen binding site thereof) and a constant region derived from a human antibody. Alternatively, a humanized antibody fragment can comprise the antigen binding site of a murine monoclonal antibody and a variable region fragment (lacking the antigen-binding site) derived from a human antibody. Procedures for the production of chimeric and further engineered monoclonal antibodies include those described in Riechmann et al. (*Nature* 332:323, 1988), Liu et al. (*PNAS* 84:3439, 1987), Larrick et al. (*Bio/Technology* 7:934, 1989), and Winter and Harris (*TIPS* 14:139, Can, 1993). Procedures to generate antibodies transgenically can be found in GB 2,272,440, U.S. Pat. Nos. 5,569,825 and 5,545,806 and related patents claiming priority therefrom, all of which are incorporated by reference herein. Preferably, for use in humans, the antibodies are human or humanized; techniques for creating such human or humanized antibodies are also well known and are commercially available from, for example, Medarex Inc. (Princeton, N.J.) and Abgennix Inc. (Fremont, Calif.).

Antigen-binding antibody fragments which recognize specific epitopes may be generated by known techniques. For example, such fragments include but are not limited to: the F(ab')2 fragments which can be produced by pepsin digestion of the antibody molecule and the Fab fragments which can be generated by reducing the disulfide bridges of the (ab')2 fragments. Alternatively, Fab expression libraries may be constructed (Huse et al., 1989, Science, 246:1275–1281) to allow rapid and easy identification of monoclonal Fab fragments with the desired specificity. Techniques described for the production of single chain antibodies (U.S. Pat No. 4,946,778; Bird, 1988, Science 242:423–426; Huston et al., 1988, Proc. Natl. Acad. Sci. USA 85:5879–5883; and Ward et al., 1989, Nature 334: 544–546) can also be adapted to produce single chain antibodies against human Claudin-19, -21, and -22 gene products. Single chain antibodies are formed by linking the heavy and light chain fragments of the Fv region via an amino acid bridge, resulting in a single chain polypeptide. In addition, antibodies to the human Claudin-19, -21, and -22 polypeptide can, in turn, be utilized to generate anti-idiotype antibodies that "mimic" the human Claudin-19, -21, and -22 polypeptide and that may bind to the human Claudin-19, -21, and -22 polypeptide using techniques well known to those skilled in the art. (See, e.g., Greenspan & Bona, 1993, FASEB J 7(5):437–444; and Nissinoff, 1991, J. Immunol. 147(8):2429–2438).

Screening procedures by which such antibodies can be identified are well known, and can involve immunoaffinity chromatography, for example. Antibodies can be screened for agonistic (i.e., ligand-mimicking) properties. Such antibodies, upon binding to cell surface human Claudin-19, -21, and -22, induce biological effects (e.g., transduction of biological signals) similar to the biological effects induced when the human Claudin-19, -21, and -22 binding partner binds to cell surface human Claudin-19, -21, and -22. Agonistic antibodies can be used to induce human Claudin-19, -21, and -22-mediate stimulatory pathways or intercellular communication.

Those antibodies that can block binding of the Claudin polypeptides of the invention of the invention to binding partners for human Claudin-19, -21, and -22 can be used to inhibit human Claudin-19, -21, and -22-mediated intercellular communication or co-stimulation that results from such binding. Such blocking antibodies can be identified using any suitable assay procedure, such as by testing antibodies for the ability to inhibit binding of human Claudin-19, -21, and -22 binding to certain cells expressing a human Claudin-19, -21, and -22 binding partner. Alternatively, blocking antibodies can be identified in assays for the ability to inhibit a biological effect that results from binding of human Claudin-19, -21, and -22 to target cells. Antibodies can be assayed for the ability to inhibit human Claudin-19, -21, and -22 binding partner-mediated stimulatory pathways, for example. Such an antibody can be employed in an in vitro procedure, or administered in vivo to inhibit a biological activity mediated by the entity that generated the antibody. Disorders caused or exacerbated (directly or indirectly) by the interaction of human Claudin-19, -21, and -22 with cell surface binding partner receptor thus can be treated. A therapeutic method involves in vivo administration of a blocking antibody to a mammal in an amount effective in inhibiting human Claudin-19, -21, and -22 binding partner-mediated biological activity. Monoclonal antibodies are generally preferred for use in such therapeutic methods. In one embodiment, an antigen-binding antibody fragment is employed. Compositions comprising an antibody that is directed against human Claudin-19, -21, and -22, and a physiologically acceptable diluent, excipient, or carrier, are provided herein. Suitable components of such compositions are as described below for compositions containing Claudin polypeptides of the invention.

Also provided herein are conjugates comprising a detectable (e.g., diagnostic) or therapeutic agent, attached to the antibody. Examples of such agents are presented above. The conjugates find use in in vitro or in vivo procedures. The antibodies of the invention can also be used in assays to detect the presence of the polypeptides or fragments of the invention, either in vitro or in vivo. The antibodies also can be employed in purifying polypeptides or fragments of the invention by immunoaffinity chromatography.

Rational Design of Compounds that Interact with Claudin Polypeptides of the Invention The goal of rational drug design is to produce structural analogs of biologically active polypeptides of interest or of small molecules with which they interact, e.g., inhibitors, agonists, antagonists, etc. Any of these examples can be used to fashion drugs which are more active or stable forms of the polypeptide or which enhance or interfere with the function of a polypeptide in vivo (Hodgson J (1991) Biotechnology 9:19–21, incorporated herein by reference). In one approach, the three-dimensional structure of a polypeptide of interest, or of a polypeptide-inhibitor complex, is determined by x-ray crystallography, by nuclear magnetic resonance, or by computer homology modeling or, most typically, by a combination of these approaches. Both the shape and charges of the polypeptide must be ascertained to elucidate the structure and to determine active site(s) of the molecule. Less often, useful information regarding the structure of a polypeptide may be gained by modeling based on the structure of homologous polypeptides. In both cases, relevant structural information is used to design analogous serpin-like molecules, to identify efficient inhibitors, or to identify small molecules that may bind serpins. Useful examples of rational drug design may include molecules which have improved activity or stability as shown by Braxton S and Wells J A (1992 Biochemistry 31:7796–7801) or which act as inhibitors, agonists, or antagonists of native peptides as shown by Athauda S B et al (1993 J Biochem 113:742–746), incorporated herein by reference. The use of human Claudin-19, -21, and -22 polypeptide structural information in molecular modeling software systems to assist in inhibitor design and inhibitor-human Claudin-19, -21, and -22 polypeptide interaction is also encompassed by the invention. A particular method of the invention comprises analyzing the three dimensional structure of Claudin polypeptides of the invention for likely binding sites of substrates, synthesizing a new molecule that incorporates a predictive reactive site, and assaying the new molecule as described further herein.

It is also possible to isolate a target-specific antibody, selected by functional assay, as described-further herein, and then to solve its crystal structure. This approach, in principle, yields a pharmacore upon which subsequent drug design can be based. It is possible to bypass polypeptide crystallography altogether by generating anti-idiotypic antibodies (anti-ids) to a functional, pharmacologically active antibody. As a mirror image of a mirror image, the binding site of the anti-ids would be expected to be an analog of the original receptor. The anti-id could then be used to identify and isolate peptides from banks of chemically or biologically produced peptides. The isolated peptides would then act as the pharmacore.

Assays of Activities of Claudin Polypeptides of the Invention

The purified Claudin polypeptides of the invention of the invention (including polypeptides, polypeptides, fragments, variants, oligomers, and other forms) are useful in a variety of assays. For example, the human Claudin-19, -21, and -22 molecules of the present invention can be used to identify binding partners of Claudin polypeptides of the invention, which can also be used to modulate intercellular communication or cell activity. Alternatively, they can be used to identify non-binding-partner molecules or substances that modulate intercellular communication or cell activity.

Assays to Identify Binding Partners. Polypeptides of the human Claudin-19, -21, and -22 and fragments thereof can be used to identify binding partners. For example, they can be tested for the ability to bind a candidate binding partner in any suitable assay, such as a conventional binding assay. To illustrate, the human Claudin-19, -21, and -22 polypeptide can be labeled with a detectable reagent (e.g., a radionuclide, chromophore, enzyme that catalyzes a colorimetric or fluorometric reaction, and the like). The labeled polypeptide is contacted with cells expressing the candidate binding partner. The cells then are washed to remove unbound labeled polypeptide, and the presence of cell-bound label is determined by a suitable technique, chosen according to the nature of the label.

One example of a binding assay procedure is as follows. A recombinant expression vector containing the candidate binding partner cDNA is constructed. CV1-EBNA-1 cells in 10 cm$^2$ dishes are transfected with this recombinant expression vector. CV-1/EBNA-1 cells (ATCC CRL 10478) constitutively express EBV nuclear antigen-1 driven from the CMV Immediate-early enhancer/promoter. CV1-EBNA-1 was derived from the African Green Monkey kidney cell line CV-1 (ATCC CCL 70), as described by McMahan et al., (*EMBO J.* 10:2821, 1991). The transfected cells are cultured for 24 hours, and the cells in each dish then are split into a 24-well plate. After culturing an additional 48 hours, the transfected cells (about 4×10$^4$ cells/well) are washed with BM-NFDM, which is binding medium (RPMI 1640 containing 25 mg/ml bovine serum albumin, 2 mg/ml sodium azide, 20 mM Hepes pH 7.2) to which 50 mg/ml nonfat dry milk has been added. The cells then are incubated for 1 hour at 37° C. with various concentrations of, for example, a soluble polypeptide/Fc fusion polypeptide made as set forth above. Cells then are washed and incubated with a constant saturating concentration of a $^{125}$I-mouse anti-human IgG in binding medium, with gentle agitation for 1 hour at 37° C. After extensive washing, cells are released via trypsinization. The mouse anti-human IgG employed above is directed against the Fc region of human IgG and can be obtained from Jackson Immunoresearch Laboratories, Inc., West Grove, Pa. The antibody is radioiodinated using the standard chloramine-T method. The antibody will bind to the Fc portion of any polypeptide/Fc polypeptide that has bound to the cells. In all assays, non-specific binding of $^{125}$I-antibody is assayed in the absence of the Fc fusion polypeptide/Fc, as well as in the presence of the Fc fusion polypeptide and a 200-fold molar excess of unlabeled mouse anti-human IgG antibody. Cell-bound $^{125}$I-antibody is quantified on a Packard Autogamma counter. Affinity calculations (Scatchard, *Ann. N.Y. Acad. Sci.* 51:660, 1949) are generated on RS/1 (BBN Software, Boston, Mass.) run on a Microvax computer. Binding can also be detected using methods that are well suited for high-throughput screening procedures, such as scintillation proximity assays (Udenfriend S, Gerber L D, Brink L, Spector S, 1985, Proc Natl Acad Sci USA 82: 8672–8676), homogeneous time-resolved fluorescence methods (Park Y W, Cummings R T, Wu L, Zheng S, Cameron P M, Woods A, Zaller D M, Marcy A I, Hermes J D, 1999, Anal Biochem 269: 94–104), fluorescence resonance energy transfer (FRET) methods (Clegg R M, 1995, Curr Opin Biotechnol 6: 103–110), or methods that measure any changes in surface plasmon resonance when a bound polypeptide is exposed to a potential binding partner, such methods using for example a biosensor such as that supplied by Biacore AB (Uppsala, Sweden).

Yeast Two-Hybrid or "Interaction Trap" Assays. Where the human Claudin-19, -21, and -22 polypeptide binds or potentially binds to another polypeptide (such as, for example, in a receptor-ligand interaction), the nucleic acid encoding the human Claudin-19, -21, and -22 polypeptide can also be used in interaction trap assays (such as, for example, that described in Gyuris et al., Cell 75:791–803 (1993)) to identify nucleic acids encoding the other polypeptide with which binding occurs or to identify inhibitors of the binding interaction. Polypeptides involved in these binding interactions can also be used to screen for peptide or small molecule inhibitors or agonists of the binding interaction.

Competitive Binding Assays. Another type of suitable binding assay is a competitive binding assay. To illustrate, biological activity of a variant can be determined by assaying for the variant's ability to compete with the native polypeptide for binding to the candidate binding partner. Competitive binding assays can be performed by conventional methodology. Reagents that can be employed in competitive binding assays include radiolabeled human Claudin-19, -21, and -22 and intact cells expressing human Claudin-19, -21, and -22 (endogenous or recombinant) on the cell surface. For example, a radiolabeled soluble human Claudin-19, -21, and -22 fragment can be used to compete with a soluble human Claudin-19, -21, and -22 variant for binding to cell surface receptors. Instead of intact cells, one could substitute a soluble binding partner/Fc fusion polypeptide bound to a solid phase through the interaction of Polypeptide A or Polypeptide G (on the solid phase) with the Fc moiety. Chromatography columns that contain Polypeptide A and Polypeptide G include those available from Pharmacia Biotech, Inc., Piscataway, N.J.

Assays to Identify Modulators of Intercellular Communication or Cell Activity. The influence of Claudin polypeptides of the invention on intercellular communication or cell activity can be manipulated to control these activities in target cells. For example, the disclosed Claudin polypeptides of the invention, nucleic acids encoding the disclosed Claudin polypeptides of the invention, or agonists or antagonists of such polypeptides can be administered to a cell or group of cells to induce, enhance, suppress, or arrest cellular communication or activity in the target cells. Identification of Claudin polypeptides of the invention, agonists or antagonists that can be used in this manner can be carried out via a variety of assays known to those skilled in the art. Included in such assays are those that evaluate the ability of an human Claudin-19, -21, and -22 polypeptide to influence intercellular communication or cell activity. Such an assay would involve, for example, the analysis of cell interaction in the presence of an human Claudin-19, -21, and -22 polypeptide. In such an assay, one would determine a rate of communication or cell stimulation in the presence of the human Claudin-19, -21, and -22 polypeptide and then determine if such communication or cell stimulation is altered in the presence of a candidate agonist or antagonist or another human Claudin-19, -21, and -22 polypeptide. Exemplary assays for this aspect of the invention include cytokine secretion assays, T-cell co-stimulation assays, and mixed lymphocyte reactions involving antigen presenting cells and T cells. These assays are well known to those skilled in the art.

In another aspect, the present invention provides a method of detecting the ability of a test compound to affect the intercellular communication or co-stimulatory activity of a cell. In this aspect, the method comprises: (1) contacting a first group of target cells with a test compound including an human Claudin-19, -21, and -22 receptor polypeptide or fragment thereof under conditions appropriate to the particular assay being used; (2) measuring the net rate of intercellular communication or co-stimulation among the target cells; and (3) observing the net rate of intercellular communication or co-stimulation among control cells containing the human Claudin-19, -21, and -22 receptor polypeptides or fragments thereof, in the absence of a test compound, under otherwise identical conditions as the first group of cells. In this embodiment, the net rate of intercellular communication or co-stimulation in the control cells is compared to that of the cells treated with both the human Claudin-19, -21, and -22 molecule as well as a test compound. The comparison will provide a difference in the net rate of intercellular communication or co-stimulation such that an effector of intercellular communication or co-stimulation can be identified. The test compound can function as an effector by either activating or up-regulating, or by inhibiting or down-regulating intercellular communication or co-stimulation, and can be detected through this method.

Cell Proliferation, Cell Death. Cell Differentiation. and Cell Adhesion Assays. A polypeptide of the present invention may exhibit cytokine, cell proliferation (either inducing or inhibiting) or cell differentiation (either inducing or inhibiting activity or may induce production of other cytokines in certain cell populations. Many polypeptide factors discovered to date, including all known cytokines, have exhibited activity in one or more factor dependent cell proliferation assays, and hence the assays serve as a convenient confirmation of cytokine activity. The activity of a polypeptide of the present invention is evidenced by any one of a number of routine factor dependent cell proliferation assays for cell lines including, without limitation, 32D, DA2, DA1G, T10, B9, B9/11, BaF3, MC9/G, M+ (preB M+), 2E8, RB5, DA1, 123, T1165, HT2, CTLL2, TF-1, Mo7e and CMK. The activity of a human Claudin-19, -21, and -22 polypeptide of the invention may, among other means, be measured by the following methods:

Assays for cell movement and adhesion include, without limitation, those described in: Current Protocols in Immunology, Ed by J. E. Coligan, A. M. Kruisbeek, D. H. Margulies, E. M. Shevach, W. Strober, Pub. Greene Publishing Associates and Wiley-Interscience (Chapter 6.12, Measurement of alpha and beta Chemokines 6.12.1–6.12.28; Taub et al. J. Clin. Invest. 95:1370–1376, 1995; Lind et al. APMIS 103:140–146, 1995; Muller et al Eur. J. Immunol. 25: 1744–1748; Gruber et al. J. of Immunol. 152:5860–5867, 1994; Johnston et al. J. of Immunol. 153: 1762–1768, 1994

Assays for cadherin adhesive and invasive suppressor activity include, without limitation, those described in: Hortsch et al. J Biol Chem 270 (32): 18809–18817, 1995; Miyaki et al. Oncogene 11: 2547–2552, 1995; Ozawa et al. Cell 63:1033–1038, 1990.

Diagnostic and other Uses of Claudin Polypeptides of the Invention and Nucleic Acids The nucleic acids encoding the Claudin polypeptides of the invention provided by the present invention can be used for numerous diagnostic or other useful purposes. The nucleic acids of the invention can be used to express recombinant polypeptide for analysis, characterization or therapeutic use; as markers for tissues in which the corresponding polypeptide is preferentially expressed (either constitutively or at a particular stage of tissue differentiation or development or in disease states); as molecular weight markers on Southern gels; as chromosome markers or tags (when labeled) to identify chromosomes or to map related gene positions; to compare with endogenous DNA sequences in patients to identify potential genetic disorders; as probes to hybridize and thus discover novel, related DNA sequences; as a source of information to derive PCR primers for genetic fingerprinting; as a probe to "subtract-out" known sequences in the process of discovering other novel nucleic acids; for selecting and making oligomers for attachment to a "gene chip" or other support, including for examination of expression patterns; to raise anti-polypeptide antibodies using DNA immunization techniques; as an antigen to raise anti-DNA antibodies or elicit another immune response, and for gene therapy. Uses of Claudin polypeptides of the invention and fragmented polypeptides include, but are not limited to, the following: purifying polypeptides and measuring the activity thereof; delivery agents; therapeutic and research reagents; molecular weight and isoelectric focusing markers; controls for peptide fragmentation; identification of unknown polypeptides; and preparation of antibodies. Any or all nucleic acids suitable for these uses are capable of being developed into reagent grade or kit format for commercialization as products. Methods for performing the uses listed above are well known to those skilled in the art. References disclosing such methods include without limitation "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R Kimmel eds., 1987

Probes and Primers. Among the uses of the disclosed human Claudin-19, -21, and -22 nucleic acids, and combinations of fragments thereof, is the use of fragments as probes or primers. Such fragments generally comprise at least about 17 contiguous nucleotides of a DNA sequence. In other embodiments, a DNA fragment comprises at least 30, or at least 60, contiguous nucleotides of a DNA sequence. The basic parameters affecting the choice of hybridization conditions and guidance for devising suitable conditions are set forth by Sambrook et al., 1989 and are described in detail above. Using knowledge of the genetic code in combination with the amino acid sequences set forth above, sets of degenerate oligonucleotides can be prepared. Such oligonucleotides are useful as primers, e.g., in polymerase chain reactions (PCR), whereby DNA fragments are isolated and amplified. In certain embodiments, degenerate primers can be used as probes for non-human genetic libraries. Such libraries would include but are not limited to cDNA libraries, genomic libraries, and even electronic EST (express sequence tag) or DNA libraries. Homologous sequences identified by this method would then be used as probes to identify non-human human Claudin-19, -21, and -22 homologues.

Chromosome Mapping. The nucleic acids encoding Claudin polypeptides of the invention, and the disclosed fragments and combinations of these nucleic acids, can be used by those skilled in the art using well-known techniques to identify the human chromosome to which these nucleic acids map. Useful techniques include, but are not limited to, using the sequence or portions, including oligonucleotides, as a probe in various well-known techniques such as radiation hybrid mapping (high resolution), in situ hybridization to chromosome spreads (moderate resolution), and Southern blot hybridization to hybrid cell lines containing individual human chromosomes (low resolution). For example, chromosomes can be mapped by radiation hybridization. First, PCR is performed using the Whitehead Institute/MIT Center for Genome Research Genebridge4 panel of 93 radiation hybrids: www-genome.wi.mit.edu/ftp/distribution/human_STS_releases/july97/rhmap/genebridge4.html. Primers are used which lie within a putative exon of the gene of interest and which amplify a product from human genomic DNA, but do not amplify hamster genomic DNA. The results of the PCRs are converted into a data vector that is submitted to the Whitehead/MIT Radiation Mapping site on the internet (www-seq.wi.mit.edu). The data is scored and the chromosomal assignment and placement relative to known Sequence Tag Site (STS) markers on the radiation hybrid map is provided. The following web site provides additional information about radiation hybrid mapping: www-genome.wi.mit.edu/ftp/distribution/human_STS_releases/july97/07-97.INTRO.html.

Diagnostics and Gene Therapy. The nucleic acids encoding Claudin polypeptides of the invention, and the disclosed fragments and combinations of these nucleic acids can be used by one skilled in the art using well-known techniques to analyze abnormalities associated with the genes corresponding to these polypeptides. This enables one to distinguish conditions in which this marker is rearranged or deleted. In addition, nucleic acids of the invention or a fragment thereof can be used as a positional marker to map other genes of unknown location. The DNA can be used in developing treatments for any disorder mediated (directly or indirectly) by defective, or insufficient amounts of, the genes corresponding to the nucleic acids of the invention. Disclosure herein of native nucleotide sequences permits the detection of defective genes, and the replacement thereof with normal genes. Defective genes can be detected in in vitro diagnostic assays, and by comparison of a native nucleotide sequence disclosed herein with that of a gene derived from a person suspected of harboring a defect in this gene.

Methods of Screening for Binding Partners. The Claudin polypeptides of the invention of the invention each can be used as reagents in methods to screen for or identify binding partners. For example, the Claudin polypeptides of the invention can be attached to a solid support material and may bind to their binding partners in a manner similar to affinity chromatography. In particular embodiments, a polypeptide is attached to a solid support by conventional procedures. As one example, chromatography columns containing functional groups that will react with functional groups on amino acid side chains of polypeptides are available (Pharmacia Biotech, Inc., Piscataway, N.J.). In an alternative, a polypeptide/Fc polypeptide (as discussed above) is attached to Polypeptide A- or Polypeptide G-containing chromatography columns through interaction with the Fc moiety. The Claudin polypeptides of the invention also find use in identifying cells that express a binding partner on the cell surface. Polypeptides are bound to a solid phase such as a column chromatography matrix or a similar suitable substrate. For example, magnetic microspheres can be coated with the polypeptides and held in an incubation vessel through a magnetic field. Suspensions of cell mixtures containing potential binding-partner-expressing cells are contacted with the solid phase having the polypeptides thereon. Cells expressing the binding partner on the cell surface bind to the fixed polypeptides, and unbound cells are washed away. Alternatively, Claudin polypeptides of the invention can be conjugated to a detectable moiety, then incubated with cells to be tested for binding partner expression. After incubation, unbound labeled matter is removed and the presence or absence of the detectable moiety on the cells is determined. In a further alternative, mixtures of cells suspected of expressing the binding partner are incubated with biotinylated polypeptides. Incubation periods are typically at least one hour in duration to ensure sufficient binding. The resulting mixture then is passed through a column packed with avidin-coated beads, whereby the high affinity of biotin for avidin provides binding of the desired cells to the beads. Procedures for using avidin-coated beads are known (see Berenson, et al. *J. Cell. Biochem.*, 10D:239, 1986). Washing to remove unbound material, and the release of the bound cells, are performed using conventional methods. In some instances, the above methods for screening for or identifying binding partners may also be used or modified to isolate or purify such binding partner molecules or cells expressing them.

Measuring Biological Activity. Polypeptides also find use in measuring the biological activity of human Claudin-19, -21, and -22-binding polypeptides in terms of their binding affinity. The polypeptides thus can be employed by those conducting "quality assurance" studies, e.g., to monitor shelf life and stability of polypeptide under different conditions. For example, the polypeptides can be employed in a binding affinity study to measure the biological activity of a binding partner polypeptide that has been stored at different temperatures, or produced in different cell types. The polypeptides also can be used to determine whether biological activity is retained after modification of a binding partner polypeptide (e.g., chemical modification, truncation, mutation, etc.). The binding affinity of the modified polypeptide is compared to that of an unmodified binding polypeptide to detect any adverse impact of the modifications on biological activity of the binding polypeptide. The biological activity of a binding polypeptide thus can be ascertained before it is used in a research study, for example.

Carriers and Delivery Agents. The polypeptides also find use as carriers for delivering agents attached thereto to cells bearing identified binding partners. The polypeptides thus can be used to deliver diagnostic or therapeutic agents to such cells (or to other cell types found to express binding partners on the cell surface) in vitro or in vivo procedures. Detectable (diagnostic) and therapeutic agents that can be attached to a polypeptide include, but are not limited to, toxins, other cytotoxic agents, drugs, radionuclides, chromophores, enzymes that catalyze a calorimetric or fluorometric reaction, and the like, with the particular agent being chosen according to the intended application. Among the toxins are ricin, abrin, diphtheria toxin, *Pseudomonas aeruginosa* exotoxin A, ribosomal inactivating polypeptides, mycotoxins such as trichothecenes, and derivatives and fragments (e.g., single chains) thereof. Radionuclides suitable for diagnostic use include, but are not limited to, $^{123}$I, $^{131}$I, $^{99m}$Tc, $^{111}$In, and $^{76}$Br. Examples of radionuclides suitable for therapeutic use are $^{131}$I, $^{211}$At, $^{77}$Br, $^{186}$Re, $^{188}$Re, $^{212}$Pb, $^{212}$Bi, $^{109}$Pd, $^{64}$Cu, and $^{67}$Cu. Such agents can be attached to the polypeptide by any suitable conventional procedure. The polypeptide comprises functional groups on amino acid side chains that can be reacted with functional groups on a desired agent to form covalent bonds, for example. Alternatively, the polypeptide or agent can be derivatized to generate or attach a desired reactive functional group. The derivatization can involve attachment of one of the bifunctional coupling reagents available for attaching various molecules to polypeptides (Pierce Chemical Company, Rockford, Ill.). A number of techniques for radiolabeling polypeptides are known. Radionuclide metals can be attached to polypeptides by using a suitable bifunctional chelating agent, for example. Conjugates comprising polypeptides and a suitable diagnostic or therapeutic agent (preferably covalently linked) are thus prepared. The conjugates are administered or otherwise employed in an amount appropriate for the particular application.

Treating Diseases with Claudin Polypeptides of the Invention and Antagonists Thereof It is anticipated that the Claudin polypeptides of the invention, fragments, variants, antagonists, agonists, antibodies, and binding partners of the invention will be useful for treating medical conditions and diseases including, but not limited to, conditions involving epithelial or endothelial barrier function or ion transport as described further herein. The therapeutic molecule or molecules to be used will depend on the etiology of the condition to be treated and the biological pathways involved, and variants, fragments, and binding partners of Claudin polypeptides of the invention may have effects similar to or different from Claudin polypeptides of the invention. For example, an antagonist of the tight junction formation activity of Claudin polypeptides of the invention may be selected for treatment of conditions involving tight junction formation, but a particular fragment of a given human Claudin-19, -21, and -22 polypeptide may also act as an effective dominant negative antagonist of that activity. Therefore, in the following paragraphs "Claudin polypeptides of the invention or antagonists" refers to all Claudin polypeptides of the invention, fragments, variants, antagonists, agonists, antibodies, and binding partners etc. of the invention, and it is understood that a specific molecule or molecules can be selected from those provided as embodiments of the invention by individuals of skill in the art, according to the biological and therapeutic considerations described herein.

The disclosed Claudin polypeptides of the invention or antagonists, compositions and combination therapies described herein are useful in medicines for treating bacterial, viral or protozoal infections, and complications resulting therefrom. One such disease is *Mycoplasma pneumonia*. In addition, provided herein is the use of Claudin polypeptides of the invention or antagonists to treat AIDS and related conditions, such as AIDS dementia complex, AIDS associated wasting, lipidistrophy due to antiretroviral therapy; and Kaposi's sarcoma. Provided herein is the use of Claudin polypeptides of the invention or antagonists for treating protozoal diseases, including malaria and schistosomiasis. Additionally provided is the use of Claudin polypeptides of the invention or antagonists to treat erythema nodosum leprosum; bacterial or viral meningitis; tuberculosis, including pulmonary tuberculosis; and pneumonitis secondary to a bacterial or viral infection. Provided also herein is the use of Claudin polypeptides of the invention or antagonists to prepare medicaments for treating louse-borne relapsing fevers, such as that caused by *Borrelia recurrentis*. The Claudin polypeptides of the invention or antagonists of the invention can also be used to prepare a medicament for treating conditions caused by Herpes viruses, such as herpetic stromal keratitis, corneal lesions, and virus-induced corneal disorders. In addition, Claudin polypeptides of the invention or antagonists can be used in treating human papillomavirus infections. The Claudin polypeptides of the invention or antagonists of the invention are used also to prepare medicaments to treat influenza.

Cardiovascular disorders are treatable with the disclosed Claudin polypeptides of the invention or antagonists, pharmaceutical compositions or combination therapies, including aortic aneurisms; arteritis; vascular occlusion, including cerebral artery occlusion; complications of coronary by-pass surgery; ischemia/reperfusion injury; heart disease, including atherosclerotic heart disease, myocarditis, including chronic autoimmune myocarditis and viral myocarditis; heart failure, including chronic heart failure (CHF), cachexia of heart failure; myocardial infarction; restenosis after heart surgery; silent myocardial ischemia; post-implantation complications of left ventricular assist devices; Raynaud's phenomena; thrombophlebitis; vasculitis, including Kawasaki's vasculitis; giant cell arteritis, Wegener's granulomatosis; and Schoenlein-Henoch purpura.

A combination of at least one human Claudin-19, -21, and -22 polypeptide or antagonist and one or more other anti-angiogenesis factors may be used to treat solid tumors, thereby reducing the vascularization that nourishes the tumor tissue. Suitable anti-angiogenic factors for such combination therapies include IL-8 inhibitors, angiostatin, endostatin, kringle 5, inhibitors of vascular endothelial growth factor (such as antibodies against vascular endothelial growth factor), angiopoietin-2 or other antagonists of angiopoietin-1, antagonists of platelet-activating factor and antagonists of basic fibroblast growth factor In addition, the subject Claudin polypeptides of the invention or antagonists, compositions and combination therapies are used to treat chronic pain conditions, such as chronic pelvic pain, including chronic prostatitis/pelvic pain syndrome. As a further example, Claudin polypeptides of the invention or antagonists and the compositions and combination therapies of the invention are used to treat postherpetic pain.

Provided also are methods for using Claudin polypeptides of the invention or antagonists, compositions or combination therapies to treat various disorders of the endocrine system. For example, the Claudin polypeptides of the invention or antagonists are used to treat juvenile onset diabetes (includes autoimmune and insulin-dependent types of diabetes) and also to treat maturity onset diabetes (includes non-insulin dependent and obesity-mediated diabetes). In addition, the subject compounds, compositions and combination therapies are used to treat secondary conditions associated with diabetes, such as diabetic retinopathy, kidney transplant rejection in diabetic patients, obesity-mediated insulin resistance, and renal failure, which itself may be associated with proteinurea and hypertension. Other endocrine disorders also are treatable with these compounds, compositions or combination therapies, including polycystic ovarian disease, X-linked adrenoleukodystrophy, hypothyroidism and thyroiditis, including Hashimoto's thyroiditis (i.e., autoimmune thyroiditis).

Conditions of the gastrointestinal system also are treatable with Claudin polypeptides of the invention or antagonists, compositions or combination therapies, including coeliac disease. In addition, the compounds, compositions and combination therapies of the invention are used to treat Crohn's disease; ulcerative colitis; idiopathic gastroparesis; pancreatitis, including chronic pancreatitis and lung injury associated with acute pancreatitis; and ulcers, including gastric and duodenal ulcers.

Included also are methods for using the subject Claudin polypeptides of the invention or antagonists, compositions or combination therapies for treating disorders of the genitourinary system, such as glomerulonephritis, including autoimmune glomerulonephritis, glomerulonephritis due to exposure to toxins or glomerulonephritis secondary to infections with haemolytic streptococci or other infectious agents. Also treatable with the compounds, compositions and combination therapies of the invention are uremic syndrome and its clinical complications (for example, renal failure, anemia, and hypertrophic cardiomyopathy), including uremic syndrome associated with exposure to environmental toxins, drugs or other causes. Further conditions treatable with the compounds, compositions and combination therapies of the invention are complications of hemodialysis; prostate conditions, including benign prostatic hypertrophy, nonbacterial prostatitis and chronic prostatitis; and complications of hemodialysis.

Also provided herein are methods for using Claudin polypeptides of the invention or antagonists, compositions or combination therapies to treat various hematologic and oncologic disorders. For example, Claudin polypeptides of the invention or antagonists are used to treat various forms of cancer, including acute myelogenous leukemia, Epstein-Barr virus-positive nasopharyngeal carcinoma, glioma, colon, stomach, prostate, renal cell, cervical and ovarian cancers, lung cancer (SCLC and NSCLC), including cancer-associated cachexia, fatigue, asthenia, paraneoplastic syndrome of cachexia and hypercalcemia. Additional diseases treatable with the subject Claudin polypeptides of the invention or antagonists, compositions or combination therapies are solid tumors, including sarcoma, osteosarcoma, and carcinoma, such as adenocarcinoma (for example, breast cancer) and squamous cell carcinoma. In addition, the subject compounds, compositions or combination therapies are useful for treating leukemia, including acute myelogenous leukemia, chronic or acute lymphoblastic leukemia and hairy cell leukemia Other malignancies with invasive metastatic potential can be treated with the subject compounds, compositions and combination therapies, including multiple myeloma. In addition, the disclosed Claudin polypeptides of the invention or antagonists, compositions and combination therapies can be used to treat anemias and hematologic disorders, including anemia of chronic disease, aplastic anemia, including Fanconi's aplastic anemia; idiopathic thrombocytopenic purpura (ITP); myelodysplastic syndromes (including refractory anemia, refractory anemia with ringed sideroblasts, refractory anemia with excess blasts, refractory anemia with excess blasts in transformation); myelofibrosis/myeloid metaplasia; and sickle cell vasocclusive crisis.

Other conditions treatable by the disclosed Claudin polypeptides of the invention or antagonists, compositions and combination therapies include those resulting from injuries to the head or spinal cord, and including subdural hematoma due to trauma to the head.

The disclosed Claudin polypeptides of the invention or antagonists, compositions and combination therapies are further used to treat conditions of the liver such as hepatitis, including acute alcoholic hepatitis, acute drug-induced or viral hepatitis, hepatitis A, B and C, sclerosing cholangitis and inflammation of the liver due to unknown causes.

A number of pulmonary disorders also can be treated with the disclosed Claudin polypeptides of the invention or antagonists, compositions and combination therapies. One such condition is adult respiratory distress syndrome (ARDS), which may be triggered by a variety of causes, including exposure to toxic chemicals, pancreatitis, trauma or other causes. The disclosed compounds, compositions and combination therapies of the invention also are useful for treating broncho-pulmonary dysplasia (BPD); lymphangioleiomyomatosis; and chronic fibrotic lung disease of preterm infants. In addition, the compounds, compositions and combination therapies of the invention are used to treat occupational lung diseases, including asbestosis, coal worker's pneumoconiosis, silicosis or similar conditions associated with long-term exposure to fine particles. In other aspects of the invention, the disclosed compounds, compositions and combination therapies are used to treat pulmonary disorders, including chronic obstructive pulmonary disease (COPD) associated with chronic bronchitis or emphysema; fibrotic lung diseases, such as cystic fibrosis, idiopathic pulmonary fibrosis and radiation-induced pulmonary fibrosis; pulmonary sarcoidosis; and allergies, including allergic rhinitis, contact dermatitis, atopic dermatitis and asthma.

The Claudin polypeptides of the invention or antagonists of the invention, optionally combined with the cytokine IFNγ-1b (such as ACTIMMUNE®; InterMune Pharmaceuticals) may be used for treating cystic fibrosis or fibrotic lung diseases, such as idiopathic pulmonary fibrosis, radiation-induced pulmonary fibrosis and bleomycin-induced pulmonary fibrosis. In addition, this combination is useful for treating other diseases characterized by organ fibrosis, including systemic sclerosis (also called "scleroderma"), which often involves fibrosis of the liver. For treating cystic fibrosis, Claudin polypeptides of the invention or antagonists and IIFNγ-1b may be combined with PULMOZYME® (dornase alfa) Inhalation Solution or TOBI® (tobramycin solution for inhalation) or other treatments for cystic fibrosis.

The Claudin polypeptides of the invention or antagonists of the invention alone or in combination with IFNγ-1b may be administered together with other treatments presently used for treating fibrotic lung disease. Such additional treatments include glucocorticoids, azathioprine, cyclophosphamide, penicillamine, colchisicine, supplemental oxygen and so forth. Patients with fibrotic lung disease, such as IPF, often present with nonproductive cough, progressive dyspnea, and show a restrictive ventilatory pattern in pulmonary function tests. Chest radiographs reveal fibrotic accumulations in the patient's lungs. When treating fibrotic lung disease in accord with the disclosed methods, sufficiency of treatment may be detected by observing a decrease in the patient's coughing (when cough is present), or by using standard lung function tests to detect improvements in total lung capacity, vital capacity, residual lung volume or by administering a arterial blood gas determination measuring desaturation under exercising conditions, and showing that the patient's lung function has improved according to one or more of these measures. In addition, patient improvement may be determined through chest radiography results showing that the progression of fibrosis in the patient's lungs has become arrested or reduced.

In addition, Claudin polypeptides of the invention or antagonists (including soluble Claudin polypeptides of the invention or antibodies against Claudin polypeptides of the invention) are useful for treating organ fibrosis when administered in combination with relaxin, a hormone that down-regulates collagen production thus inhibiting fibrosis, or when given in combination with agents that block the fibrogenic activity of TGF-β. Combination therapies using Claudin polypeptides of the invention or antagonists and recombinant human relaxin are useful, for example, for treating systemic sclerosis or fibrotic lung diseases, including cystic fibrosis, idiopathic pulmonary fibrosis, radiation-induced pulmonary fibrosis and bleomycin-induced pulmonary fibrosis.

Other embodiments provide methods for using the disclosed Claudin polypeptides of the invention or antagonists, compositions or combination therapies to treat a variety of rheumatic disorders. These include: adult and juvenile rheumatoid arthritis; systemic lupus erythematosus; gout; osteoarthritis; polymyalgia rheumatica; seronegative spondylarthropathies, including ankylosing spondylitis; and Reiter's disease. The subject Claudin polypeptides of the invention or antagonists, compositions and combination therapies are used also to treat psoriatic arthritis and chronic Lyme arthritis. Also treatable with these compounds, compositions and combination therapies are Still's disease and uveitis associated with rheumatoid arthritis. In addition, the compounds, compositions and combination therapies of the invention are used in treating disorders resulting in inflammation of the voluntary muscle, including dermatomyositis and polymyositis. In addition, the compounds, compositions and combinations disclosed herein are used to treat multicentric reticulohistiocytosis, a disease in which joint destruction and papular nodules of the face and hands are associated with excess production of proinflammatory cytokines by multinucleated giant cells.

The Claudin polypeptides of the invention or antagonists, compositions and combination therapies of the invention are useful for treating primary amyloidosis. In addition, the secondary amyloidosis that is characteristic of various conditions also are treatable with Claudin polypeptides of the invention or antagonists such as Claudin polypeptides of the invention or antagonists, and the compositions and combination therapies described herein. Such conditions include: Alzheimer's disease, secondary reactive amyloidosis; Down's syndrome; and dialysis-associated amyloidosis.

Also treatable with the compounds, compositions and combination therapies of the invention are inherited periodic fever syndromes, including familial Mediterranean fever, hyperimmunoglobulin D and periodic fever syndrome and TNF-receptor associated periodic syndromes (TRAPS).

Disorders associated with transplantation also are treatable with the disclosed Claudin polypeptides of the invention or antagonists, compositions or combination therapies, such as graft-versus-host disease, and complications resulting from solid organ transplantation, including transplantion of heart, liver, lung, skin, kidney or other organs. Claudin polypeptides of the invention or antagonists may be administered, for example, to prevent or inhibit the development of bronchiolitis obliterans after lung transplantation.

Ocular disorders also are treatable with the disclosed Claudin polypeptides of the invention or antagonists, compositions or combination therapies, including rhegmatogenous retinal detachment, and inflammatory eye disease, and inflammatory eye disease associated with smoking and macular degeneration.

The Claudin polypeptides of the invention or antagonists of the invention and the disclosed compositions and combination therapies also are useful for treating disorders that affect the female reproductive system. Examples include, but are not limited to, multiple implant failure/infertility; fetal loss syndrome or IV embryo loss (spontaneous abortion); preeclamptic pregnancies or eclampsia; and endometriosis.

The disclosed Claudin polypeptides of the invention or antagonists, compositions and combination therapies furthermore are useful for treating acute polyneuropathy; anorexia nervosa; Bell's palsy; chronic fatigue syndrome; transmissible dementia, including Creutzfeld-Jacob disease; demyelinating neuropathy; Guillain-Barre syndrome; vertebral disc disease; Gulf war syndrome; myasthenia gravis; silent cerebral ischemia; sleep disorders, including narcolepsy and sleep apnea; chronic neuronal degeneration; and stroke, including cerebral ischemic diseases.

Disorders involving the skin or mucous membranes also are treatable using the disclosed Claudin polypeptides of the invention or antagonists, compositions or combination therapies. Such disorders include acantholytic diseases, including Darier's disease, keratosis follicularis and pemphigus vulgaris. Also treatable with the subject Claudin polypeptides of the invention or antagonists, compositions and combination therapies are acne; acne rosacea; alopecia areata; aphthous stomatitis; bullous pemphigoid; burns; eczema; erythema, including erythema multiforme and erythema multiforme bullosum (Stevens-Johnson syndrome); inflammatory skin disease; lichen planus; linear IgA bullous disease (chronic bullous dermatosis of childhood); loss of skin elasticity; mucosal surface ulcers; neutrophilic dermatitis (Sweet's syndrome); pityriasis rubra pilaris; psoriasis; pyoderma gangrenosum; and toxic epidermal necrolysis.

Administration of Claudin Polypeptides of the Invention and Antagonists Thereof

This invention provides compounds, compositions, and methods for treating a patient, preferably a mammalian patient, and most preferably a human patient, who is suffering from a medical disorder, and in particular a human Claudin-19, -21, and -22-mediated disorder. Such human Claudin-19, -21, and -22-mediated disorders include conditions caused (directly or indirectly) or exacerbated by binding between human Claudin-19, -21, and -22 and a binding partner. For purposes of this disclosure, the terms "illness,"

"disease," "medical condition," "abnormal condition" and the like are used interchangeably with the term "medical disorder." The terms "treat", "treating", and "treatment" used herein includes curative, preventative (e.g., prophylactic) and palliative or ameliorative treatment For such therapeutic uses, Claudin polypeptides of the invention and fragments, human Claudin-19, -21, and -22 nucleic acids encoding the Claudin polypeptides of the invention, and/or agonists or antagonists of the human Claudin-19, -21, and -22 polypeptide such as antibodies can be administered to the patient in need through well-known means. Compositions of the present invention can contain a polypeptide in any form described herein, such as native polypeptides, variants, derivatives, oligomers, and biologically active fragments. In particular embodiments, the composition comprises a soluble polypeptide or an oligomer comprising soluble Claudin polypeptides of the invention.

Therapeutically Effective Amount. In practicing the method of treatment or use of the present invention, a therapeutically effective amount of a therapeutic agent of the present invention is administered to a patient having a condition to be treated, preferably to treat or ameliorate diseases associated with the activity of a human Claudin-19, -21, and -22 polypeptide. "Therapeutic agent" includes without limitation any of the Claudin polypeptides of the invention, fragments, and variants; nucleic acids encoding the Claudin polypeptides of the invention, fragments, and variants; agonists or antagonists of the Claudin polypeptides of the invention such as antibodies; human Claudin-19, -21, and -22 polypeptide binding partners; complexes formed from the Claudin polypeptides of the invention, fragments, variants, and binding partners, etc. As used herein, the term "therapeutically effective amount" means the total amount of each therapeutic agent or other active component of the pharmaceutical composition or method that is sufficient to show a meaningful patient benefit, i.e., treatment, healing, prevention or amelioration of the relevant medical condition, or an increase in rate of treatment, healing, prevention or amelioration of such conditions. When applied to an individual therapeutic agent or active ingredient, administered alone, the term refers to that ingredient alone. When applied to a combination, the term refers to combined amounts of the ingredients that result in the therapeutic effect, whether administered in combination, serially or simultaneously. As used herein, the phrase "administering a therapeutically effective amount" of a therapeutic agent means that the patient is treated with said therapeutic agent in an amount and for a time sufficient to induce an improvement, and preferably a sustained improvement, in at least one indicator that reflects the severity of the disorder. An improvement is considered "sustained" if the patient exhibits the improvement on at least two occasions separated by one or more weeks. The degree of improvement is determined based on signs or symptoms, and determinations may also employ questionnaires that are administered to the patient, such as quality-of-life questionnaires. Various indicators that reflect the extent of the patient's illness may be assessed for determining whether the amount and time of the treatment is sufficient. The baseline value for the chosen indicator or indicators is established by examination of the patient prior to administration of the first dose of the therapeutic agent. Preferably, the baseline examination is done within about 60 days of administering the first dose. If the therapeutic agent is being administered to treat acute symptoms, the first dose is administered as soon as practically possible after the injury has occurred. Improvement is induced by administering therapeutic agents such as Claudin polypeptides of the invention or antagonists until the patient manifests an improvement over baseline for the chosen indicator or indicators. In treating chronic conditions, this degree of improvement is obtained by repeatedly administering this medicament over a period of at least a month or more, e.g., for one, two, or three months or longer, or indefinitely. A period of one to six weeks, or even a single dose, often is sufficient for treating acute conditions. For injuries or acute conditions, a single dose may be sufficient. Although the extent of the patient's illness after treatment may appear improved according to one or more indicators, treatment may be continued indefinitely at the same level or at a reduced dose or frequency. Once treatment has been reduced or discontinued, it later may be resumed at the original level if symptoms should reappear.

Dosing. One skilled in the pertinent art will recognize that suitable dosages will vary, depending upon such factors as the nature and severity of the disorder to be treated, the patient's body weight, age, general condition, and prior illnesses and/or treatments, and the route of administration. Preliminary doses can be determined according to animal tests, and the scaling of dosages for human administration is performed according to art-accepted practices such as standard dosing trials. For example, the therapeutically effective dose can be estimated initially from cell culture assays. The dosage will depend on the specific activity of the compound and can be readily determined by routine experimentation. A dose may be formulated in animal models to achieve a circulating plasma concentration range that includes the IC50 (i.e., the concentration of the test compound which achieves a half-maximal inhibition of symptoms) as determined in cell culture, while minimizing toxicities. Such information can be used to more accurately determine useful doses in humans. Ultimately, the attending physician will decide the amount of polypeptide of the present invention with which to treat each individual patient Initially, the attending physician will administer low doses of polypeptide of the present invention and observe the patient's response. Larger doses of polypeptide of the present invention may be administered until the optimal therapeutic effect is obtained for the patient, and at that point the dosage is not increased further. It is contemplated that the various pharmaceutical compositions used to practice the method of the present invention should contain about 0.01 ng to about 100 mg (preferably about 0.1 ng to about 10 mg, more preferably about 0.1 microgram to about 1 mg) of polypeptide of the present invention per kg body weight. In one embodiment of the invention, Claudin polypeptides of the invention or antagonists are administered one time per week to treat the various medical disorders disclosed herein, in another embodiment is administered at least two times per week, and in another embodiment is administered at least three times per week. If injected, the effective amount of Claudin polypeptides of the invention or antagonists per adult dose ranges from 1–20 mg/m$^2$, and preferably is about 5–12 mg/m$^2$. Alternatively, a flat dose may be administered, whose amount may range from 5–100 mg/dose. Exemplary dose ranges for a flat dose to be administered by subcutaneous injection are 5–25 mg/dose, 25–50 mg/dose and 50–100 mg/dose. In one embodiment of the invention, the various indications described below are treated by administering a preparation acceptable for injection containing Claudin polypeptides of the invention or antagonists at 25 mg/dose, or alternatively, containing 50 mg per dose. The 25 mg or 50 mg dose may be administered repeatedly, particularly for chronic conditions. If a route of administration other than injection is used, the dose is appropriately adjusted in accord with standard medical practices. In many instances, an improvement in a patient's condition will be obtained by injecting a dose of about 25 mg of Claudin polypeptides of the invention or antagonists one to three times per week over a period of at least three weeks, or a dose of 50 mg of Claudin polypeptides of the invention or antagonists one or two times per week for at least three weeks, though treatment for longer periods may be necessary to induce the desired degree of improvement. For incurable chronic conditions, the regimen may be continued indefinitely, with adjustments being made to dose and frequency if such are deemed necessary by the patient's physician. The foregoing doses are examples for an adult patient who is a person who is 18 years of age or older. For pediatric patients (age 4–17), a suitable regimen involves the subcutaneous injection of 0.4 mg/kg, up to a maximum dose of 25 mg of Claudin polypeptides of the invention or antagonists, administered by subcutaneous injection one or more times per week If an antibody against a human Claudin-19, -21, and -22 polypeptide is used as the human Claudin-19, -21, and -22 polypeptide antagonist, a preferred dose range is 0.1 to 20 mg/kg, and more preferably is 1–10 mg/kg. Another preferred dose range for an anti-human Claudin-19, -21, and -22 polypeptide antibody is 0.75 to 75 mg/kg of body weight. Humanized antibodies are preferred, that is, antibodies in which only the antigen-binding portion of the antibody molecule is derived from a non-human source. Such antibodies may be injected or administered intravenously.

Formulations. Compositions comprising an effective amount of a human Claudin-19, -21, and -22 polypeptide of the present invention (from whatever source derived, including without limitation from recombinant and non-recombinant sources), in combination with other components such as a physiologically acceptable diluent, carrier, or excipient, are provided herein. The term "pharmaceutically acceptable" means a non-toxic material that does not interfere with the effectiveness of the biological activity of the active ingredient(s). Formulations suitable for administration include aqueous and non-aqueous sterile injection solutions which may contain anti-oxidants, buffers, bacteriostats and solutes which render the formulation isotonic with the blood of the recipient; and aqueous and non-aqueous sterile suspensions which may include suspending agents or thickening agents. The polypeptides can be formulated according to known methods used to prepare pharmaceutically useful compositions. They can be combined in admixture, either as the sole active material or with other known active materials suitable for a given indication, with pharmaceutically acceptable diluents (e.g., saline, Tris-HCl, acetate, and phosphate buffered solutions), preservatives (e.g., thimerosal, benzyl alcohol, parabens), emulsifiers, solubilizers, adjuvants and/or carriers. Suitable formulations for pharmaceutical compositions include those described in *Remington's Pharmaceutical Sciences*, 16th ed. 1980, Mack Publishing Company, Easton, Pa. In addition, such compositions can be complexed with polyethylene glycol (PEG), metal ions, or incorporated into polymeric compounds such as polyacetic acid, polyglycolic acid, hydrogels, dextran, etc., or incorporated into liposomes, microemulsions, micelles, unilamellar. or multilamellar vesicles, erythrocyte ghosts or spheroblasts. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. No. 4,235,871; U.S. Pat. No. 4,501,728; U.S. Pat. No. 4,837,028; and U.S. Pat. No. 4,737,323, all of which are incorporated herein by reference. Such compositions will influence the physical state, solubility, stability, rate of in vivo release, and rate of in vivo clearance, and are thus chosen according to the intended application, so that the characteristics of the carrier will depend on the selected route of administration. In one preferred embodiment of the invention, sustained-release forms of Claudin polypeptides of the invention are used. Sustained-release forms suitable for use in the disclosed methods include, but are not limited to, Claudin polypeptides of the invention that are encapsulated in a slowly-dissolving biocompatible polymer (such as the alginate microparticles described in U.S. Pat. No. 6,036,978), admixed with such a polymer (including topically applied hydrogels), and or encased in a biocompatible semi-permeable implant.

Combinations of Therapeutic Compounds. A human Claudin-19, -21, and -22 polypeptide of the present invention may be active in multimers (e.g., heterodimers or homodimers) or complexes with itself or other polypeptides. As a result, pharmaceutical compositions of the invention may comprise a polypeptide of the invention in such multimeric or complexed form. The pharmaceutical composition of the invention may be in the form of a complex of the polypeptide(s) of present invention along with polypeptide or peptide antigens. The invention further includes the administration of Claudin polypeptides of the invention or antagonists concurrently with one or more other drugs that are administered to the same patient in combination with the Claudin polypeptides of the invention or antagonists, each drug being administered according to a regimen suitable for that medicament. "Concurrent administration" encompasses simultaneous or sequential treatment with the components of the combination, as well as regimens in which the drugs are alternated, or wherein one component is administered long-term and the other(s) are administered intermittently. Components may be administered in the same or in separate compositions, and by the same or different routes of administration. Examples of components that may be included in the pharmaceutical composition of the invention are: cytokines, lymphokines, or other hematopoietic factors such as M-CSF, GM-CSF, TNF, IL-1, IL-2, IL-3, IL4, IL5, IL-6, IL-7, IL-8, IL-9, IL-10, IL-11, IL-12, IL-13, IL-14, IL-15, IL-17, IL-18, IFN, TNF0, TNF1, TNF2, G-CSF, Meg-CSF, thrombopoietin, stem cell factor, and erythropoietin. The pharmaceutical composition may further contain other agents which either enhance the activity of the polypeptide or compliment its activity or use in treatment. Such additional factors and/or agents may be included in the pharmaceutical composition to produce a synergistic effect with polypeptide of the invention, or to minimize side effects. Conversely, a human Claudin-19, -21, and -22 polypeptide or antagonist of the present invention may be included in formulations of the particular cytokine, lymphokine, other hematopoietic factor, thrombolytic or anti-thrombotic factor, or anti-inflammatory agent to minimize side effects of the cytokine, lymphokine, other hematopoietic factor, thrombolytic or anti-thrombotic factor, or anti-inflammatory agent. Additional examples of drugs to be administered concurrently include but are not limited to antivirals, antibiotics, analgesics, corticosteroids, antagonists of inflammatory cytokines, non-steroidal anti-inflammatories, pentoxifylline, thalidomide, and disease-modifying antirheumatic drugs (DMARDs) such as azathioprine, cyclophosphamide, cyclosporine, hydroxychloroquine sulfate, methotrexate, leflunomide, minocycline, penicillamine, sulfasalazine and gold compounds such as oral gold, gold sodium thiomalate, and aurothioglucose. Additionally, Claudin polypeptides of the invention or antagonists may be combined with a second human Claudin-19, -21, and -22 polypeptide/antagonist, including an antibody against a human Claudin-19, -21, and -22 polypeptide, or a human Claudin-19, -21, and -22 polypeptide-derived peptide that acts as a competitive inhibitor of a native human Claudin-19, -21, and -22 polypeptide.

Routes of Administration. Any efficacious route of administration may be used to therapeutically administer Claudin polypeptides of the invention or antagonists thereof, including those compositions comprising nucleic acids. Parenteral administration includes injection, for example, via intra-articular, intravenous, intramuscular, intralesional, intraperitoneal or subcutaneous routes by bolus injection or by continuous infusion., and also includes localized administration, e.g., at a site of disease or injury. Other suitable means of administration include sustained release from implants; aerosol inhalation and/or insufflation.; eyedrops; vaginal or rectal suppositories; buccal preparations; oral preparations, including pills, syrups, lozenges or chewing gum; and, topical preparations such as lotions, gels, sprays, ointments or other suitable techniques. Alternatively, polypeptideaceous Claudin polypeptides of the invention or antagonists may be administered by implanting cultured cells that express the polypeptide, for example, by implanting cells that express Claudin polypeptides of the invention or antagonists. Cells may also be cultured ex vivo in the presence of polypeptides of the present invention in order to proliferate or to produce a desired effect on or activity in such cells. Treated cells can then be introduced in vivo for therapeutic purposes. In another embodiment, the patient's own cells are induced to produce Claudin polypeptides of the invention or antagonists by transfection in vivo or ex vivo with a DNA that encodes Claudin polypeptides of the invention or antagonists. This DNA can be introduced into the patient's cells, for example, by injecting naked DNA or liposome-encapsulated DNA that encodes Claudin polypeptides of the invention or antagonists, or by other means of transfection. Nucleic acids of the invention may also be administered to patients by other known methods for introduction of nucleic acid into a cell or organism (including, without limitation, in the form of viral vectors or naked DNA). When Claudin polypeptides of the invention or antagonists are administered in combination with one or more other biologically active compounds, these may be administered by the same or by different routes, and may be administered simultaneously, separately or sequentially.

Oral Administration. When a therapeutically effective amount of polypeptide of the present invention is administered orally, polypeptide of the present invention will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% polypeptide of the present invention, and preferably from about 25 to 90% polypeptide of the present invention. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of polypeptide of the present invention, and preferably from about 1 to 50% polypeptide of the present invention.

Intravenous Administration. When a therapeutically effective amount of polypeptide of the present invention is administered by intravenous, cutaneous or subcutaneous injection, polypeptide of the present invention will be in the form of a pyrogen-free, parenterally acceptable aqueous solution. The preparation of such parenterally acceptable polypeptide solutions, having due regard to pH, isotonicity, stability, and the like, is within the skill in the art. A preferred pharmaceutical composition for intravenous, cutaneous, or subcutaneous injection should contain, in addition to polypeptide of the present invention, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additives known to those of skill in the art. The duration of intravenous therapy using the pharmaceutical composition of the present invention will vary, depending on the severity of the disease being treated and the condition and potential idiosyncratic response of each individual patient. It is contemplated that the duration of each application of the polypeptide of the present invention will be in the range of 12 to 24 hours of continuous intravenous administration. Ultimately the attending physician will decide on the appropriate duration of intravenous therapy using the pharmaceutical composition of the present invention.

Bone and Tissue Administration. For compositions of the present invention which are useful for bone, cartilage, tendon or ligament regeneration, the therapeutic method includes administering the composition topically, systematically, or locally as an implant or device. When administered, the therapeutic composition for use in this invention is, of course, in a pyrogen-free, physiologically acceptable form. Further, the composition may desirably be encapsulated or injected in a viscous form for delivery to the site of bone, cartilage or tissue damage. Topical administration may be suitable for wound healing and tissue repair. Therapeutically useful agents other than a polypeptide of the invention which may also optionally be included in the composition as described above, may alternatively or additionally, be administered simultaneously or sequentially with the composition in the methods of the invention. Preferably for bone and/or cartilage formation, the composition would include a matrix capable of delivering the polypeptide-containing composition to the site of bone and/or cartilage damage, providing a structure for the developing bone and cartilage and optimally capable of being resorbed into the body. Such matrices may be formed of materials presently in use for other implanted medical applications. The choice of matrix material is based on biocompatibility, biodegradability, mechanical properties, cosmetic appearance and interface properties. The particular application of the compositions will define the appropriate formulation. Potential matrices for the compositions may be biodegradable and chemically defined calcium sulfate, tricalciumphosphate, hydroxyapatite, polylactic acid, polyglycolic acid and polyanhydrides. Other potential materials are biodegradable and biologically well-defined, such as bone or dermal collagen. Further matrices are comprised of pure polypeptides or extracellular matrix components. Other potential matrices are nonbiodegradable and chemically defined, such as sintered hydroxapatite, bioglass, alurninates, or other ceramics Matrices may be comprised of combinations of any of the above mentioned types of material, such as polylactic acid and hydroxyapatite or collagen and tricalciumphosphate. The bioceramics may be altered in composition, such as in calcium-aluminate-phosphate and processing to alter pore size, particle size, particle shape, and biodegradability. Presently preferred is a 50:50 (mole weight) copolymer of lactic acid and glycolic acid in the form of porous particles having diameters ranging from 150 to 800 microns. In some applications, it will be useful to utilize a sequestering agent, such as carboxymethyl cellulose or autologous blood clot, to prevent the polypeptide compositions from disassociating from the matrix. A preferred family of sequestering agents is cellulosic materials such as alkylcelluloses (including hydroxyalkylcelluloses), including methylcellulose, ethylcellulose, hydroxyethylcellulose, hydroxypropylcellulose, hydroxypropyl-methylcellulose, and carboxymethyl-cellulose, the most preferred being cationic salts of carboxymethylcellulose (CMC). Other preferred sequestering agents include hyaluronic acid, sodium alginate, poly(ethylene glycol), polyoxyethylene oxide, carboxyvinyl polymer and poly (vinyl alcohol). The amount of sequestering agent useful herein is 0.5–20 wt %, preferably 1–10 wt % based on total formulation weight, which represents the amount necessary to prevent desorbtion of the polypeptid from the polymer matrix and to provide appropriate handling of the composition, yet not so much that the progenitor cells are prevented from infiltrating the matrix, thereby providing the polypeptide the opportunity to assist the osteogenic activity of the progenitor cells. In further compositions, polypeptides of the invention may be combined with other agents beneficial to the treatment of the bone and/or cartilage defect, wound, or tissue in question. These agents include various growth factors such as epidermal growth factor (EGF), platelet derived growth factor (PDGF), transforming growth factors (TGF-.alpha. and TGF-.beta.), and insulin-like growth factor (IGF). The therapeutic compositions are also presently valuable for veterinary applications. Particularly domestic animals and thoroughbred horses, in addition to humans, are desired patients for such treatment with polypeptides of the present invention. The dosage regimen of a polypeptide-containing pharmaceutical composition to be used in tissue regeneration will be determined by the attending physician considering various factors which modify the action of the polypeptides, e.g., amount of tissue weight desired to be formed, the site of damage, the condition of the damaged tissue, the size of a wound, type of damaged tissue (e.g., bone), the patients age, sex, and diet, the severity of any infection, time of administration and other clinical factors. The dosage may vary with the type of matrix used in the reconstitution and with inclusion of other polypeptides in the pharmaceutical composition. For example, the addition of other known growth factors, such as IGF I (insulin like growth factor I), to the final composition, may also effect the dosage. Progress can be monitored by periodic assessment of tissue/bone growth and/or repair, for example, X-rays, histomorphometric determinations and tetracycline labeling.

Veterinary Uses. In addition to human patients, Claudin polypeptides of the invention and antagonists are useful in the treatment of disease conditions in non-human animals, such as pets (dogs, cats, birds, primates, etc.), domestic farm animals (horses cattle, sheep, pigs, birds, etc.), or any animal that suffers from a TNFα-mediated inflammatory or arthritic condition. In such instances, an appropriate dose may be determined according to the animal's body weight For example, a dose of 0.2–1 mg/kg may be used. Alternatively, the dose is determined according to the animal's surface area, an exemplary dose ranging from 0.1–20 mg/m$^2$, or more preferably, from 5–12 mg/m$^2$. For small animals, such as dogs or cats, a suitable dose is 0.4 mg/kg. In a preferred embodiment, Claudin polypeptides of the invention or antagonists (preferably constructed from genes derived from the same species as the patient), is administered by injection or other suitable route one or more times per week until the animal's condition is improved, or it may be administered indefinitely.

Manufacture of Medicaments. The present invention also relates to the use Claudin polypeptides of the invention, fragments, and variants; nucleic acids encoding the Claudin polypeptides of the invention, fragments, and variants; agonists or antagonists of the Claudin polypeptides of the invention such as antibodies; human Claudin-19, -21, and -22 polypeptide binding partners; complexes formed from the Claudin polypeptides of the invention, fragments, variants, and binding partners, etc, in the manufacture of a medicament for the prevention or therapeutic treatment of each medical disorder disclosed herein.

EXAMPLES

The following examples are intended to illustrate particular embodiments and not to limit the scope of the invention.

Example 1

Identification of Human Claudin Polypeptides

A data set was received from Celera Genomics (Rockville, Md.) containing a listing of amino acid sequences predicted to be encoded by the human genome. This data set was searched with a BLAST algorithm to identify Claudin family polypeptides. Two overlapping amino acid sequences (SEQ ID NO:1 and SEQ ID NO:2) were identified as being partial amino acid sequences of a new human Claudin polypeptide, Claudin-21. SEQ ID NO:1 was used in a TBLASTN search of human genomic DNA sequences to identify two overlapping genomic DNA fragments; a contig formed from these two fragments is shown as SEQ ID NO:3. Nucleotides 2 to 592 of SEQ ID NO:3 encode an amino acid sequence, SEQ ID NO:4, that overlaps with SEQ ID NO:1 and extends it at both ends. However, comparison of the N-terminal amino acid sequence of SEQ ID NO:4 with that of SEQ ID NO:2 and other Claudin family polypeptides suggested that there was a frameshift in the nucleotide sequence of SEQ ID NO:3. When one of the 'a' residues at nucleotides 40–42 of SEQ ID NO:3 is deleted, the result is SEQ ID NO:5; nucleotides 1 to 405 of SEQ ID NO:5 encode amino acids 24 to 158 of SEQ ID NO:2. Extending the amino acid sequence of SEQ ID NO:2 using the amino acids encoded by nucleotides 406 to 591 of SEQ ID NO:5 produces SEQ ID NO:6, which is the predicted amino acid sequence of the full-length Claudin-21 polypeptide. (Nucleotides 1 to 591 of SEQ ID NO:5 encode amino acids 24 to 220 of SEQ ID NO:6). The difference between the N-terminal regions of SEQ ID NO:4 and SEQ ID NO:6 may represent an allelic variation between nucleic acids encoding these amino acid sequences. A mouse amino acid sequence (SEQ ID NO:7) has been identified that shows a high degree of sequence similarity to both the human Claudin-21 (SEQ ID NO:6) and the human Claudin-22 (SEQ ID NO:11) polypeptides; this mouse polypeptide is referred to herein as 'murine Claudin-21' because is it somewhat more similar to human Claudin-21 than to human Claudin-22.

We identified human Claudin-19 (SEQ ID NO:8) within the data automatically generated by the Sanger Centre's Ensembl Project (ensembl.org) as gene ENSG00000066018, and we appear to be the first to identify this polypeptide as a human Claudin polypeptide, having Claudin polypeptide activity, and being the human homologue of the partial murine Claudin-19 sequence (SEQ ID NO:9). In addition, a variant of the human Claudin-19 polypeptide sequence was identified (SEQ ID NO:10); this variant has an sequence of amino acids 19 through 33 of SEQ ID NO:10 in place of amino acids 19 through 38 of SEQ ID NO:8, possibly as a result of allelic or splice variation. We identified amino acid sequences comprised by human Claudin-22 (SEQ ID NO:11) within data automatically generated by Celera, and we appear to be the first to identify these polypeptide sequences as human Claudin polypeptides, having Claudin polypeptide activity.

The amino acid sequences of human Claudin-19 (SEQ ID NO:8), murine Claudin-19 (SEQ ID NO:9), the variant of human Claudin-19 (SEQ ID NO:10), human Claudin-21 (SEQ ID NO:6), the variant of human Claudin-21 (SEQ ID NO:4), murine "Claudin-21" (SEQ ID NO:7), and human Claudin-22 (SEQ ID NO:11) were compared with the amino acid sequences of other Claudin family members such as Claudin-1 (SEQ ID NO:12) and Claudin-7 (SEQ ID NO:13), as shown in Table 1 below. This comparison used the GCG "pretty" multiple sequence alignment program, with amino acid similarity scoring matrix=blosum62, gap creation penalty=8, and gap extension penalty=2. The alignment of these sequences shown in Table 1 shows capitalized concensus residues which are identical among at least five of the amino acid sequences in the alignment. Human Claudin-21 shows about 36–40% amino acid identity to other Claudin polypeptide family members, and about 54–57% amino acid similarity (based on the blosum62 comparison matrix).

Amino acid substitutions and other alterations (deletions, insertions, etc.) to the Claudin polypeptides of the invention are predicted to be more likely to alter or disrupt Claudin polypeptide activities if they result in changes to the capitalized residues shown in Table 1, and particularly if those changes do not substitute a residue present in other Claudin polypeptides at that conserved position. Conversely, if a change is made to a Claudin amino acid sequence resulting in substitution of one or more Table 1 consensus sequence residues for the Claudin polypeptide residue at that conserved position, it is less likely that such an alteration will affect Claudin polypeptide function. For example, the consensus residue at position 50 in Table 1 is tyrosine, and some Claudin polypeptides have a threonine or an isoleucine at that position. Substitution of threonine or an isoleucine or chemically similar residues such as serine or one of the aliphatic amino acids at that position is considered less likely to alter the function of the polypeptide than substitution of charged residues such as lysine or arginine etc.

Embodiments of the invention include Claudin polypeptides and fragments of Claudin polypeptides comprising altered amino acid sequences. Altered Claudin-19, -21, or -22 polypeptide sequences share at least 30%, or more preferably at least 40%, or more preferably at least 50%, or more preferably at least 55%, or more preferably at least 60%, or more preferably at least 65%, or more preferably at least 70%, or more preferably at least 75%, or more preferably at least 80%, or more preferably at least 85%, or more preferably at least 90%, or more preferably at least 95%, or more preferably at least 97.5%, or more preferably at least 99%, or most preferably at least 99.5% amino acid identity with a Claudin amino acid sequence shown in Table 1.

```
               SEQ ID
                       1                                                      50
Hs  cldn-1    NO:12   ~~~managlQ  LlGfiLAfLG  WigaivsTAL  PQWriysyag  dnIvTAqamY Hs  cldn-7    NO:13   ~~~mansglQ  LlGfsmALLG  WVglvacTAi  PQWqmssyag  dnIiTAqamY Hs  cldn-19   NO:8    ~~~mansglQ  LlGyfLALgG  WVgiiasTAL  PQWKqssyag  daIiTAvglY Mm  cldn-19   NO:9    ~~~~~~~~~~  ~~~yfLALgG  WVgiiasTAL  PQWKqssyag  daIiTAvglY Hs  cldn19v   NO:10   ~~~mansglQ  LlGyfLALgG  WhspatveAv  flrrlt....  .aIiTAvglY Hs  cldn-21   NO:6    malifrtamQ  svGllLsfLG  WilsiitTyL  PhWKnlnldl  nem...enwt Hs  cldn21v   NO:4    ~~~~~~~~~~  ~~~~~~~~~~  ~~~pllqlic  htgrtsnldl  nem...enwt Mm  cldn-21   NO:7    mglvfrtatQ  aaallLsLLG  WVlscltnyL  PhWKnlnlel  nem...enwt Hs  cldn-22   NO:11   mawsfrakvQ  LgGllLsLLG  WVcscvtTiL  PQWKtlnlel  nem...etwi consensus             ---------Q  L-G---LALLG WV-----TAL  PQWK------  ---I-TA---Y 51                                                    100
Hs  cldn-1    NO:12   eGLWMSCVsQ  STGqiQCKvF  DSlLnLsstL  QatRaLMVvg  ilLGviaifv Hs  cldn-7    NO:13   kGLWMdCVtQ  STGmmsCKmy  DSvLALsaaL  QatRaLMVvs  lvLGFLamfv Hs  cldn-19   NO:8    eGLWMSCasQ  STGqvQCKly  DSlLALdghi  QsaRaLMVva  vlLGFvamvl Mm  cldn-19   NO:9    eGLWMSCasQ  STGqvQCKly  DSlLALdghi  QsaRaLMVva  vlLGFvamvl Hs  cldn19v   NO:10   eGLWMSCasQ  STGqvQCKly  DSlLALd~~~  ~~~~~~~~~~  ~~~~~~~~~~

Hs  cldn-21   NO:6    mGLWqtCViQ  eevgmQCKdF  DSfLALpaeL  rvsRiLMfls  ngLGFLgllv Hs  cldn21v   NO:4    mGLWqtCViQ  eevgmQCKdF  DSfLALpaeL  rvsRiLMfls  ngLGFLgllv
```

```
            SEQ ID
Mm cldn-21  NO:7   mGLWkSCViQ  eevgrQCKdF  DSfLALpaeL  QvsRvLMslc  ngLGlLglla
Hs cldn-22  NO:11  mGiWevCVdr  eevatvCKaF  eSfLsLpqeL  QvaRiLMvas  hgLGlLglll
consensus          -GLWMSCV-Q  STG--QCK-F  DS-LAL~~~L  Q--R-LMV--  --LGFL----

101                                              150
Hs cldn-1   NO:12  atvGmkCmkc  leddevqKmR  maviGGaifl  lAGlaiLVat  aWygnriVQE
Hs cldn-7   NO:13  atmGmkCtRc  GgddvkKaR   iamgGGiifi  vAGlaaLVac  SWygHqiVtd
Hs cldn-19  NO:8   SvvGmkCtRv  GdsnpiaKgR  vaiaGGaLfi  lAGlctLtaV  SWyAtlvtQE
Mm cldn-19  NO:9   SvvGmkCtRv  GdsnptaKsR  vaisGGaLfl  lAGlctLtaV  SWyAtlvtQE
Hs cldn-21  NO:6   SgfGldClRi  GesqrdlKrR  llilGGiLsw  asGitaLVpV  SWvAHktVQE
Hs cldn21v  NO:4   SgfGldClRi  GesqrdlKrR  llilGGiLsw  asGitaLVpV  SWvAHktVQE
Mm cldn-21  NO:7   SgcGldClRl  GetqeglKkR  lltlGGtLlw  tsGvmvLVpV  SWvAHktVrE
Hs cldn-22  NO:11  csfGseCfqf  hrirwvfKrR  lgllGrtLea  sAsattLlpV  SWvAHatiQd
consensus          S--G--C-R-  G------K-R  ----GG-L--  -AG---LV-V  SW-AH--VQE 151                                              200
Hs cldn-1   NO:12  FyDpmtP.vn  aRyEFGqALF  tGWAAaslcl  LGGaLLcCsc  p..rkttsyp
Hs cldn-7   NO:13  FynpliP.tn  ikyEFGpAiF  iGWAgsalvi  LGGaLLsCsc  pgneskagyr
Hs cldn-19  NO:8   FfnpstP.vn  aRyEFGpALF  vGWAsaglav  LGGsfLcCtc  peperpns..
Mm cldn-19  NO:9   FfnpstP.vn  aRyEFGpALF  vGWAsaglam  LGGsfLcCtc  peperans..
Hs cldn-21  NO:6   FwDenvPdfv  pRwEFGeALF  lGWfAglsll  LGGcLLnCaa  csshaplalg
Hs cldn21v  NO:4   FwDenvPdfv  pRwEFGeALF  lGWfAglsll  LGGcLLnCaa  csshaplalg
Mm cldn-21  NO:7   FwDetmPeiv  pRwEFGeALF  lGWfAgfclv  LGGcvLhCaa  cwspapaass
Hs cldn-22  NO:11  FwDdsiPdii  pRwEFGgALy  lGWAAgifla  LGGlLLifsa  clgkedvpfp
consensus          F-D---P---  -R-EFG-ALF  -GWAA-----  LGG-LL-C--  ----------

201                    232
Hs cldn-1   NO:12  tprpypkpap  ssgkdyv~~~  ~~~~~~~~~~  ~~
Hs cldn-7   NO:13  aprsypk..s  nsskEyv~~~  ~~~~~~~~~~  ~~
Hs cldn-19  NO:8   spqpyrpgps  aaarEyv~~~  ~~~~~~~~~~  ~~
Mm cldn-19  NO:9   ipqpyrsgp~  ~~~~~~~~~~  ~~~~~~~~~~  ~~
Hs cldn-21  NO:6   hyavaqmqtq  cpylEdgtad  pqv~~~~~~~  ~~
Hs cldn21v  NO:4   hyavaqmqtq  cpylEdgtad  pqv~~~~~~~  ~~
Mm cldn-21  NO:7   hyavagprdh  qqhlElkqan  pei~~~~~~~  ~~
Hs cldn-22  NO:11  lmagptvpls  capvEesdgs  fhlmlrprnl  vi
consensus          ----------  ----E-----  ----------  --
```

Nucleic acid sequences encoding human Claudin-19 map to human chromosome 1p32.3. Nucleic acid sequences encoding human Claudin-21 map to human chromosome 4q35.1. Nucleic acid sequences encoding human Claudin-22 map to human chromosome 11q23.2. Nucleic acids encoding Claudin polypeptides of the invention can be used to analyze genetic abnormalities associated with these chromosomal regions, for example, enabling one of skill in the art to identify patients in which chromosomal regions comprising Claudin-encoding sequences are rearranged or deleted. There is also substantial utility in nucleic acids that can be used to confirm or to eliminate a particular genetic locus as a genetic factor for a kindred presenting with a hereditary disease.

Example 2

Expression of Human Claudin-21 Transcripts and Proteins

The expression of human Claudin-21 in different tissues was detected using RT-PCR. Claudin-21 transcripts were detected in the following human tissues: heart, kidney, lung, stomach, placenta, thymus, liver, and bone marrow, with significantly higher levels of expression observed in kidney, placenta, stomach, and heart than in other tissues.

A fusion protein comprising human Claudin-21 polypeptide and the FLAG epitope was expressed in COS cells, which were extracted with NP-40 to create an NP-40-soluble fraction and an insoluble fraction. The soluble and insoluble fractions were electrophoresed in duplicate and detected on Western blots using either antibodies specific for either the FLAG epitope or Claudin-21 polypeptide. Both antibodies detected bands of similar sizes in both the soluble and insoluble fractions, with more protein detected in the NP-40-soluble fraction but a substantial amount of protein also detected in the insoluble fraction. Insolubility in NP-40 is characteristic of proteins associated with cytoskeletal structures such as tight junctions. A portion of human Claudin-21 is present in an NP-40-insoluble fraction, even though COS cells do not form tight junctions.

The human Claudin-21-FLAG fusion protein was also expressed in CV-1 cells. When COS cells and CV1 cells expressing Claudin-21-FLAG fusion protein were treated with labeled anti-FLAG antibodies, staining was detected at regions of cell-cell contact in both the COS and CV-1 cell cultures.

Human Claudin-21 expression in human T84 intestinal epithelial cells was detected by immunoflurescence using confocal microscopy. The T84 cells were treated with red-fluorescing antibodies specific for Claudin-21 and green-fluorescing antibodies specific for ZO-1; colocalization of Claudin-21 and ZO-1 appears yellow using this method. While a varying amount of red fluorescence indicating the presence of Claudin-21 was present within the cells, an en face image of the cells showed intense yellow staining at the edges of the cells, and a vertical section through the T84 cell monolayer revealed Claudin-21 and ZO-1 colocalization at tight junctions, which appeared as yellow dots.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

SEQUENCES PRESENTED IN THE SEQUENCE LISTING

| SEQ ID NO | Sequence Type | Description |
|---|---|---|
| SEQ ID NO:1 | Amino acid | fragment of Human Claudin-21 |
| SEQ ID NO:2 | Amino acid | fragment of Human Claudin-21 |
| SEQ ID NO:3 | Nucleotide | Human genomic DNA |
| SEQ ID NO:4 | Amino acid | Variant of Human Claudin-21 encoded by SEQ ID NO:3 |
| SEQ ID NO:5 | Nucleotide | Human genomic DNA, SEQ ID NO:3 with one residue deleted |
| SEQ ID NO:6 | Amino acid | Human Claudin-21 |
| SEQ ID NO:7 | Amino acid | Murine 'Claudin-21' (GenBank AK008821) |
| SEQ ID NO:8 | Amino acid | Human Claudin-19 |
| SEQ ID NO:9 | Amino acid | Murine Claudin-19 (partial sequence, GenBank AAF98323) |
| SEQ ID NO:10 | Amino acid | Variant of Human Claudin-19 (partial sequence) |
| SEQ ID NO:11 | Amino acid | Human Claudin-22 |
| SEQ ID NO:12 | Amino acid | *Homo sapiens* Claudin-1 |
| SEQ ID NO:13 | Amino acid | *Homo sapiens* Claudin-7 |

What is claimed is:

1. An isolated polypeptide comprising the amino acid sequence of SEQ ID NO:6.

2. The polypeptide expressed by a method of expressing a polypeptide encoded by the polynucleotide consisting essentially of a nucleotide sequence encoding the amino acid sequence of claim 1, said method comprising culturing a recombinant host cell comprising the polynucleotide under conditions promoting the expression of said polypeptide.

3. The polypeptide of claim 2 in a non-glycosylated form.

* * * * *